United States Patent
Sun et al.

(10) Patent No.: US 9,205,123 B2
(45) Date of Patent: Dec. 8, 2015

(54) CAPSULE OF COMPOUND DANSHEN DRIPPING PILLS

(75) Inventors: He Sun, Tianjin (CN); Shuiping Zhou, Tianjin (CN); Lanlan Zhang, Tianjin (CN); Zhijuan Huang, Tianjin (CN); Zhaohui Song, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 0 days.

(21) Appl. No.: 13/579,762

(22) PCT Filed: Feb. 17, 2011

(86) PCT No.: PCT/CN2011/071050
§ 371 (c)(1),
(2), (4) Date: Aug. 17, 2012

(87) PCT Pub. No.: WO2011/103789
PCT Pub. Date: Sep. 1, 2011

(65) Prior Publication Data
US 2012/0315328 A1    Dec. 13, 2012

(30) Foreign Application Priority Data

Feb. 23, 2010 (CN) .......................... 2010 1 0112014

(51) Int. Cl.
| | |
|---|---|
| A61K 9/48 | (2006.01) |
| A01N 65/00 | (2009.01) |
| A61K 36/254 | (2006.01) |
| A61K 36/344 | (2006.01) |
| A61K 9/16 | (2006.01) |
| A61K 31/045 | (2006.01) |
| A61K 36/258 | (2006.01) |
| A61K 36/537 | (2006.01) |

(52) U.S. Cl.
CPC .............. *A61K 36/344* (2013.01); *A61K 9/1641* (2013.01); *A61K 9/4816* (2013.01); *A61K 31/045* (2013.01); *A61K 36/258* (2013.01); *A61K 36/537* (2013.01)

(58) Field of Classification Search
None
See application file for complete search history.

(56) References Cited

U.S. PATENT DOCUMENTS

| | | | |
|---|---|---|---|
| 3,784,684 A | 1/1974 | Friedrich et al. | |
| 2003/0152651 A1* | 8/2003 | Yan et al. | 424/728 |
| 2005/0008690 A1* | 1/2005 | Miller | 424/451 |
| 2005/0037094 A1 | 2/2005 | Yan et al. | |
| 2005/0249676 A1* | 11/2005 | Scott et al. | 424/46 |

FOREIGN PATENT DOCUMENTS

| | | |
|---|---|---|
| CN | 1066780 | 12/1992 |
| CN | 1348815 | 5/2002 |
| CN | 1463711 A | 12/2003 |
| CN | 1723998 | 1/2006 |
| CN | 1778336 A | 5/2006 |
| CN | 101717384 A * | 6/2010 |
| EP | 1658879 A1 | 5/2006 |
| EP | 1961418 A1 | 8/2008 |
| EP | 2540285 A1 | 1/2013 |
| JP | 2007504099 A | 3/2007 |
| JP | 2009515910 A | 4/2009 |

OTHER PUBLICATIONS

Wan et al, "Chemical Characteristics for Different Parts of Panax notoginseng Using Pressurized Liquid Extraction and HPLC-ELSD," Journal of Pharmaceutical and Biomedical Analysis, vol. 41, No. 5, pp. 1596-1601 (2006).*
Liu et al, "Development of the Fingerprints for the Quality of the Roots of *Salvia miltiorrhiza* and its Related Preparations by HPLC-DAD and LC—MS," Journal of Chromatography B, vol. 846, No. 1, pp. 32-41 (2007).*
English Abstract of CN 101717384 A (published on Jun. 2, 2010) (2 total pages).*
International Search Report corresponding to co-pending International Patent Application Serial No. PCT/CN2011/071050; dated May 16, 2011.
"Phamaceutical Capsules, Second edition," Pharmaceutical Press, ISBN 978 0 85369 568 4, Published 2004, Edited by Fridrun Podczeck and Brian E. Jones.
Anonymous, XP-002716771, (2010). "Danshen pills, herbal medicine for hear problems, blood circulation" Retrieved from the Internet: www.helpofchinesemedicine.com/buydanshen.htm (English Only Abstract).
Anonymous, XP-002716772, (2010). "6 Main Functions of Tasly Danshen Plus Capsule" Retrieved from the Internet: www.taslyuk.co.uk/functions.html (In English).
Li D et al, Chinese Traditional and Herbal Drugs, 40(4):544 (2009). "Preparation of Compound Danshen Sustained-release Capsula by multiparticulate time-controlled release technology" (English Only Abstract).
Liansheng et al. "The application of colouring agent and light—resistant agent in oral soft capsules" Tingjin central pharmaceutical factory No. 2, issue 1. pp. 32-34 (1997) (with translation).

\* cited by examiner

*Primary Examiner* — Dennis J Parad
(74) *Attorney, Agent, or Firm* — Nixon Peabody LLP

(57) ABSTRACT

A capsule of compound danshen dripping pills are disclosed. The color of the capsule's shell is orange, yellow, green or blue and all of these colors are in the wavelength range of 446-620 nm.

6 Claims, No Drawings

CAPSULE OF COMPOUND DANSHEN DRIPPING PILLS

CROSS-REFERENCE TO RELATED APPLICATIONS

This application is a U.S. national stage of International Patent Application No. PCT/CN2011/071050, filed Feb. 17, 2011, which claims priority of Chinese Patent Application No. 201010112014.4, filed on Feb. 23, 2010, the contents of which are each incorporated herein by reference in its entirety.

FIELD OF THE INVENTION

The present invention relates to the field of pharmaceutical preparation technology, in particular to a capsule preparation manufactured from a capsule shell with different colors and different materials.

BACKGROUND OF THE INVENTION

Compound danshen dripping pills (CSDP) are believed to be a new generation of medicine for treating cardiovascular diseases, exclusively provided by Tasly Pharmaceutical Group Co., Ltd. The CSDP is made from Traditional Chinese Medicines (TCMs) of *Radix Salvia Miltiorrhira* acting as monarch drug, *Panax Notoginseng* as minister drug and borneol as adjuvant drug, having the efficacy of removing stasis by circulating blood, relieving pain by freeing Bi and inducing resuscitation with herbal aromatics. Clinically, it has been used mainly for treating cardiovascular diseases. At present, the CSDP commercially available in Chinese market is packaged in high density polyethylene (HDPE) medicine bottle with the specifications of 180 pills/bottle, 150 pills/bottle, 100 pills/bottle and 60 pills/bottle. When used each time, 10 dripping pills are taken out from the bottle for oral administration. However, it is difficult for the patients out of China to accept this way of taking the CSDP. In order to enter the international market, the applicant planed to further develop the present CSDP into the CSDP capsule.

As an edible packaging material for food and drug, the capsule shells with different properties can produce influence upon the stability of food and drug to a certain degree. At present, the commercially available capsule shells are usually divided into two types: the gelatine capsule shell and the plant-derived capsule shell.

In terms of source, the gelatine capsule shell is mainly manufactured from collagen, a kind of protein derived from animal skin, bone and tendon purified by partial hydrolysis, and therefore a great deal of purine is contained. Fish gelatin capsule shell is a new type of gelatin capsule shell developed in recent years.

Further, the plant-derived capsule shell is mainly derived from plants, e.g. by using hydroxypropyl methyl cellulose (HPMC) as the raw material, and the raw material contains polysaccharide and the basic components of plant cell wall. At present, the common plant-derived capsule shells include as follows: the plant-derived capsule shell made from pullulan, the plant-derived capsule shell made from marine algal polysaccharide and the plant-derived capsule shell made from HPMC.

Practically, the transparent capsule shell can easily enhance the interest of using TCM, because it directly improves consumers' sensory understanding. Thus, it can be expected that the transparent capsule shell will make the TCM win the massive popularity worldwide. However, the transparent capsule shells with different colors can reflect lights at different wavelength, rendering the capsule content to be exposed to the lights having different wave energy. As a result, the transparent capsule shells with the different colors can potentially have an effect on the stability of the content to a certain extent. Likewise, the capsule shells made of different materials produce different influence on the stability of drug content because of the difference in their own hygroscopicity, stability and physicochemical properties.

In order to better achieve optimal protection for the drug content, after longtime research on the effect of capsule shells made of different materials with different colors on stability of capsules' content, the inventors of the present invention had explored and optimized some kinds of capsule shell benefiting the stability of capsules' content.

DETAILED DESCRIPTION OF THE INVENTION

The objective of the present invention is to provide a stable compound danshen dripping pills capsule.

Said capsule of the present invention consists of capsule shell; and drug content, which is loaded into said capsule shell, Characterized in that said capsule shell is a colored shell and said drug content is compound danshen dripping pills.

Preferably, the capsule shell is orange, yellow, green and blue in color with a corresponding wavelength in a range of 446-620 nm.

Further, the preferred color of the capsule shell is as follows: the orange with a corresponding wavelength in a range of 592-620 nm, the blue in a range of 446-500 nm, the yellow with a corresponding wavelength in a range of 577-592 nm and the green with a corresponding wavelength in a range of 500-577 nm.

Most preferably, the color of capsule shell is the yellow with a corresponding wavelength in a range of 577-592 nm and the green with a corresponding wavelength in a range of 500-577 nm.

According to the present invention, said capsule shell is a gelatine capsule shell or a plant-derived capsule shell.

From the viewpoint of material, preferably, said capsule shell is the plant-derived capsule shell.

According to the present invention, said CSDP is produced from three TCMs of *Radix salvia miltiorrhira, Panax notoginseng* and borneol. Preferably, relative to the total weight of the three TCMs, said CSDP is prepared from a formulation consisting of the crude drugs by the following weight percentages:

| | |
|---|---|
| *Radix salvia miltiorrhira* | 48.0%-97.0% |
| *Panax notoginseng* | 1.0%-50.0% |
| Borneol | 0.1%-3.0%. |

More preferably, relative to the total weight of the three TCMs, said CSDP is prepared from a formulation consisting of the crude drugs by weight percentages:

| | |
|---|---|
| *Radix salvia miltiorrhira* | 63.0%-94.0% |
| *Panax notoginseng* | 4.0%-35.0% |
| Borneol | 0.5%-2.0%. |

Most preferably, relative to the total weight of the three TCMs, said CSDP is prepared from a formulation consisting of the crude drugs by weight percentages:

| Radix salvia miltiorrhira | 82.87% |
| Panax notoginseng | 16.21% |
| Borneol | 0.92%. |

Herein, said crude drugs are pharmacologically active substances in the preparation, which are components different from the adjuvant. Further, said crude drugs herein refer to the unprocessed raw TCM or TCM decoction pieces. In addition, said adjuvant is a general designation of all pharmaceutically acceptable ingredients exclusive of the crude drugs. Said adjuvant is added into the formula, when designing the formula, for solving the problems of pharmaceutical preparations in formability, efficacy, stability and safety.

According to the embodiment of the present invention, before the aforesaid formulation, the crude drugs are processed by the following procedures:

Said *Radix salvia miltiorrhira* is the dry root and rhizome of dicotyledon Labiatae *Salvia miltiorrhiza* Bge, which can be cut into slices or ground, and preserved for later use.

Said *Panax notoginseng* is the dry root and rhizome of Araliaceae *Panax notoginseng* (Burk.) F. H. Chen.

Said borneol is a crystal obtained either by extraction from the processed products of the resin and the volatile oils from camphol of dipterocarpaceae or by chemical synthesis, which can be followed by being ground and screen-separated, and preserved for later use.

According to the present invention, the herbal composition can be prepared by the method known in the prior art, e.g. Chinese patent application Nos. 01136155.7, 01820875.4, 03144300.1, 200310107279.5, 200410018758.4, 200410019827.3 and 02100884.1. These patent application documents are incorporated herein by reference.

For example, the dripping pills can be prepared as follows: the crude drugs of *Radix salvia miltiorrhira* and *Panax notoginseng* are taken, extracted with boiling water or aqueous alkaline solution, and filtered. The filtrates are combined and concentrated to a certain extent. The concentrated solution is added with ethanol to perform precipitation and allowed to stand still to obtain a supernatant. Further, the obtained supernatant was concentrated by recovering the ethanol to give an extract of *Radix salvia miltiorrhira* and *Panax notoginseng*. The obtained extract was finally blended uniformly with borneol and adjuvants to prepare the dripping pill.

In particular, said CSDP can be prepared by a method comprising the following steps: the crude drugs of *Radix salvia miltiorrhira* and *Panax notoginseng* are weighed in accordance with aforesaid ratio, and reflux-extracted in water or an aqueous solution (pH 7 to 9) by heating for 2-4 times at a reflux temperature of 60-100° C. with 0.5 to 3 hours for each time. The weight of water added each time is 2-12 times the weight of the crude drugs. The obtained extract solutions are filtered and combined to give a filtrate, and the filtrate is further concentrated to an extract solution with a relative density of 1.05 to 1.25. Then, ethanol is added into the obtained extract solution to make a final ethanol content of 50%-85% (v/v), and allowed to stand still for 4-36 hours to obtain a supernatant, and the obtained supernatant is filtered to obtain a filtrate. The filtrate is concentrated by recovering the ethanol to give an extract with sugar degree of 50-90 brix, i.e. the *Radix salvia miltiorrhira* and *Panax notoginseng* extract.

The matrix adjuvant used in said CSDP according to the present invention can be polyethylene glycol-6000 (PEG-6000) having a solidifying point of 53-58° C. The weight ratio of the crude drugs to the matrix adjuvant is 1:(0.31-0.49). The afore-obtained extract and borneol have been uniformly blended with the matrix adjuvant to give a mixture. The mixture is further heated by melting (i.e. melted) and transferred to a dripping tank, where the melted mixture is dripped into a low-temperature cooling fluid (e.g. liquid paraffin). Next, after wiping off the cooling fluid, the qualified pills are selected to obtain the final product. Wherein, the melting temperature is kept at 60-100° C., and the temperature of cooling fluid is at 0-10° C., preferably 5-10° C.

Additionally, according to the present invention, said CSDP contains an adjuvant or adjuvants. The adjuvant(s) can be either a matrix adjuvant alone, or a combination of a matrix adjuvant and a plastifying adjuvant. Wherein, said matrix adjuvant can be natural matrix adjuvant derived from plant, e.g. selected from the group consisting of a pharmaceutically acceptable D-ribose, fructose, xylose, fucose, raffinose, maltose, agarose, sucrose ester, D-ribonic acid-γ-lactone, erythritol, sorbitol, xylitol, arabitol, isomaltitol, lactitol, malic acid, sterin, shellac, phenylethylene glycol, polyoxyethylene alkyl ether, and the above-mentioned compounds containing hydrate water. Besides, the matrix adjuvant can further comprise a plastifying adjuvant, e.g. selected from the group consisting of pregelatinized starch, carboxymethyl starch, arabic gum, dextran, sesbania gum, carrageenan, Indian gum, fureellaran, tragacanth gum, tamarind gum, pectin, xanthan gum, alginic acid and the salts thereof, agar, lactose, glyceryl monostearate, polyoxyethylene monostearate, cross-linked sodium carboxylmethyl cellulose and silica, etc.

According to the present invention, said CSDP can be either the coated or un-coated pill.

Wherein the said un-coated CSDP, for example, can be prepared according to following procedures:
Ingredients:
*Radix salvia miltiorrhira, Panax notoginseng* and borneol
Preparation:

Extract of *Radix salvia miltiorrhira* and *Panax notoginseng* is added with PEG-6000, the weight of the added PEG-6000 is 2.5-3.5 times the weight of the extract, and melted at a temperature of 85-90° C. Until being well-melted, the ground and screen-separated borneol is added according to the formula dosage. After homogenized mixing, the mixture is transferred to a dripping machine to drip at a temperature of 80-85° C. to give the final product.

The specific method for preparing said coated CSDPs, for example, can be as follows:
Ingredients:
*Radix salvia miltiorrhira, Panax notoginseng* and borneol
Preparation:

Extract of *Radix salvia miltiorrhira* and *Panax notoginseng* is added with PEG-6000, the weight of the added PEG-6000 is 2.5-3.5 times the weight of the extract, and melted at a temperature of 85-90° C. Until being well-melted, the ground and screen-separated borneol is added according to the formula dosage. After homogenized mixing, the mixture is transferred to a dripping machine to drip at a temperature of 80-85° C. to give un-coated dripping pills. A gastric-soluble coating material is well dissolved in water. After homogenized mixing, the un-coated dripping pills are transferred to a coating machine to conduct a coating operation under the following coating conditions according to a 6% increase in weight after coating: an average inlet air temperature of 85° C., an average coating bed temperature of 35-38° C., a spraying pressure of 2 bar, an average rotating speed of 15-23 rpm and an average material flowing rate of 3-4-g/min.

According to the present invention, some unexpected effects have been achieved and further proven by the following tests.

It should be noted that the capsule shells used for this test were purchased from Sino-US joint venture-Capsugel (Suzhou) Inc., one of the production bases of Pfizer CAPSUGEL, US.

1. Method

The capsule shells with different materials and colors loaded with CSDPs had been selected and provided as the test samples. Various test methods were adopted, e.g. HPLC, UV and GC, to assay the content change of index ingredients contained respectively in *Radix salvia miltiorrhira, Panax notoginseng* and borneol in an environment of accelerated stability test and in an environment of intensive light exposure test.

2. Apparatus and Test Sample 2.1 Apparatus

Observation box for stability test: (MMM) CLIMACELL 404 equipped with additional lighting equipment;

High performance liquid chromatography (HPLC): Agilent 1100

Ultraviolet-visible spectrophotometer: Hitachi U3010

Gas chromatograph: Agilent 8890

2.2 Test Sample 2.2.1 The CSDPs Prepared by Production Department of Tasly Pharmaceutical Group Co. Ltd.

According to the test purpose and technical feasibility, the small CSDPs with an average pill weight of 10 mg/pill had been selected as the test sample, which was prepared by the production line of Tasly Pharmaceutical Group Co. Ltd. and 30-35 pills were loaded into each common #1 capsule. The selected samples were divided into two kinds: the coated dripping pills and the un-coated dripping pills.

The dripping process of the said CSDPs is as follows:

(1) Small Un-Coated CSDPs

| | |
|---|---|
| *Radix salvia miltiorrhira* | 41.06 g |
| *Panax notoginseng* | 8.03 g |
| Borneol | 0.46 g |
| Adjuvant PEG-6000 | 18 g |

One thousand dripping pills were prepared.

Extraction of *Radix salvia miltiorrhira* and *Panax notoginseng*:

Coarsely-ground *Radix salvia miltiorrhira* and *Panax notoginseng* were placed into an extraction tank, into which water with 5 times the weight of the *Radix salvia miltiorrhira* and *Panax notoginseng* crude drugs was poured to decoct for 2 hours. After filtration of the solution, the residue was continued to be extracted for the second time. In this extraction, water with 4 times the weight of the *Radix salvia miltiorrhira* and *Panax notoginseng* crude drugs was added into the residue to decoct for 1 hour. The solution was filtered and the residue was discarded. The filtrates obtained in the above twice extraction were combined and concentrated under a reduced pressure to an extract solution with a relative density of 1.05. Then, 95% (v/v) ethanol was slowly added into the obtained extract solution to make a final ethanol content of 69%-71% (v/v), and allowed to stand still for 12 hours to separate the supernatant, and the supernatant was filtered. The filtrate was concentrated by recovering the ethanol to obtain an extract with a sugar degree of 50 brix (i.e. the *Radix salvia miltiorrhira* and *Panax notoginseng* extract).

Preparation of the Product

The afore-obtained extract was weighted, and PEG-6000 with 2.5-3.5 times the weight of the extract was added into the extract and melted at a temperature of 85-90° C. Until being well-melted, the ground and screen-separated borneol was added into the melt according to the formula dosage. After homogenized mixing, the mixture was transferred to a dripping machine to drip at a temperature of 80-85° C. to give the small un-coated CSDPs.

Specification: 10 mg/pill (average weight)

(2) Small Coated CSDPs

| | |
|---|---|
| *Radix salvia miltiorrhira* | 41.06 g |
| *Panax notoginseng* | 8.03 g |
| Borneol | 0.46 g |
| Adjuvant PEG-6000 | 18 g |

One thousand dripping pills were prepared.

Extraction of *Radix salvia miltiorrhira* and *Panax notoginseng*:

Coarsely-ground *Radix salvia miltiorrhira* and *Panax notoginseng* were placed into an extraction tank, into which an aqueous solution of sodium hydroxide (pH 9) with 5 times the weight of the *Radix salvia miltiorrhira* and *Panax notoginseng* crude drugs was poured to decoct for 2 hours. After filtration of the solution, the residue was continued to be extracted for the second time. In this extraction, the aqueous solution of sodium hydroxide (pH 9) with 4 times the weight of the *Radix salvia miltiorrhira* and *Panax notoginseng* crude drugs was added to decoct for 1 hour. The solution was filtered and the residue was discarded. The filtrates obtained in the above twice extraction were combined and concentrated under a reduced pressure to an extract with a relative density of 1.25. Then, 95% (v/v) ethanol was slowly added into the obtained extract solution to make a final ethanol content of 69%-71% (v/v), and allowed to stand still for 12 hours to separate the supernatant, and the supernatant was filtered. The filtrate was concentrated by recovering the ethanol to obtain an extract with a sugar density of 90 brix (i.e. the *Radix salvia miltiorrhira* and *Panax notoginseng* extract).

Preparation of the Product

The afore-obtained extract was weighted, and PEG-6000 with 2.5-3.5 times the weight of the extract was added into the extract and melted at a temperature of 85-90° C. Until being well-melted, the ground and screen-separated borneol was added into the melt according to the formula dosage. After homogenized mixing, the mixture was transferred to a dripping machine to drip at a temperature of 80-85° C. to give the small un-coated CSDPs.

Continuously, a gastric-soluble coating material is well dissolved in water. The obtained un-coated pills were transferred into a coating machine to conduct a coating operation under the following coating conditions according to a 6% increase in weight after coating: an average inlet air temperature of 85° C., an average coating bed temperature of 35-38° C., a spraying pressure of 2 bar, an average rotating speed of 15-23 rpm and an average material flowing rate of 3-4 g/min to give the small coated CSDPs.

Specification: 11 mg/pill (average weight)

2.2.2 Capsule Shell (Produced by Sino-US Joint Venture-Capsugel (Suzhou) Inc.)

Both gelatine capsule shells and plant-derived capsule shells were selected, totally including 16 kinds of capsule shells covering full-spectrum of visible light of red, orange, yellow, green, cyan, blue and purple (See Table 1).

TABLE 1

The serial numbers of different capsule shell materials and colors

| Color | Plant-derived capsule shell | Gelatine capsule shell | Pearlescent capsule shell | Chao'an Bao capsule shell (a type of capsule shell) |
|---|---|---|---|---|
| colorless transparent | (V43.700) | (43.801) | — | — |
| non-transparent white | (V44.700) | (44.081) | (44.650) | (44.081) |
| brown | (V06.700) | (06.802) | — | — |
| red | (V30.700) | (30.808) | — | — |
| orange | — | (20.801) | — | — |
| yellow | — | — | (39.807) | — |
| green | (V14.704) | (13.701) | — | — |
| blue | — | (02.808) | — | — |
| purple | — | (31.801) | — | — |

2.2.3 Test Sample 17 representative different combinations of the dripping pills and the capsule shells were selected and tested. Coated or un-coated dripping pills were loaded into the capsule shells made of different materials with different colors (See Table 2).

TABLE 2

Capsule shell test samples and their codes

| Serial No. | Capsule shell material and color | | Type of dripping pills | Code |
|---|---|---|---|---|
| 1 | plant-derived, non-transparent, white | | coated | ZBBB |
| 2 | | | un-coated | ZBBS |
| 3 | gelatine, colorless transparent | | coated | MWB |
| 4 | | | un-coated | MWS |
| 5 | gelatine, non-transparent, white | | coated | MBBB |
| 6 | | | un-coated | MBBS |
| 7 | gelatine, non-transparent, white, Chao'an Bao | | coated | CB |
| 8 | | | un-coated | CS |
| 9 | gelatine, non-transparent white, pearlescent | | coated | MBZBB |
| 10 | gelatine, transparent, orange | | coated | MCB |
| 11 | | | un-coated | MCS |
| 12 | gelatine | transparent, brown | coated | MZB |
| 13 | | transparent, red | coated | MHB |
| 14 | | transparent, yellow | coated | MHUB |
| 15 | | transparent, blue | coated | MLB |
| 16 | | transparent, green | coated | MGB |
| 17 | | transparent, rubylith (purple) | coated | MBHB |

3. Test Process 3.1 Test

The tests were divided into 2 parts, including an intensive light exposure test and an accelerated stability test.

3.1.1 Intensive Light Exposure Test

Intensive light exposure conditions: a temperature of 25° C., a relative humidity of 60%, an air speed of 100%. The light exposure condition is 40% light with a distance of 10 cm. The light exposure intensity is 4500 Lux. Test samples were collected on the $0^{th}$, $5^{th}$ and $10^{th}$ day.

Firstly, Samples MWB and MWS were selected to investigate whether there was any effect resulted from the lighting on the CSDP or not. Then, 9 samples of MBBB, MBZBB, MCB, MZB, MHB, MHUB, MLB, MGB and MBHB made of the same gelatine material with different colors were investigated by exposure to the intensive light to observe their protective effect on CSDPs.

3.1.2 Accelerated Stability Test

Accelerated stability test conditions: a temperature of 40° C., a relative humidity of 75%. Test samples were collected in the $0^{th}$, $1^{st}$, $2^{nd}$, $3^{rd}$, $4.5^{th}$ and $6^{th}$ month.

Coated and un-coated CSDP were loaded in the above 17 selected capsule shells made of different materials with different colors, and the variation of CSDPs were investigated during the accelerated test.

3.2 Investigation Indices in the Test

Content of the following ingredients had been determined.

Index ingredients in *Radix salvia miltiorrhira*: salvianic acid A, protocatechuic aldehyde, salvianolic acid L, salvianolic acid M, salvianolic acid D, rosmarinic acid, salvianolic acid B and salvianolic acid A;

Index ingredients in *Panax notoginseng*: R1, Rg1+Re, Rb1, Rc, Rb2, Rb3 and Rd;

Total phenolic acid, total saponin and total sugar; and borneol.

Appearance variation: the appearance variation of the dripping pills had been observed after being exposed to an extreme environment, including whether drying-crack, wet adhesion, caking, white precipitate on the surface occurred and the variation of color and pill weight.

3.3 Test Method 3.3.1 Fingerprint Graph of *Radix salvia miltiorrhira* and Method for Content Determination 3.3.1.1 Preparation of Test Sample Respectively, 10 CSDPs in each sample were weighted and placed in 10 ml volumetric flasks, added with a proper amount of distilled water, dissolved by ultrasound for 15 min and diluted to the 10 ml. The obtained solution was centrifugally filtered. Two parallel samples were prepared. Injection volume of each sample was 10 ul.

Standard substances of salvianic acid A, protocatechuic aldehyde, salvianolic acid L, salvianolic acid M, salvianolic acid D, rosmarinic acid, salvianolic acid B and salvianolic acid A were weighed respectively to prepare the standard solutions. Injection volume of each sample was 10 ul.

3.3.1.2 HPLC Method

Agilent SB-C18 analytical column (4.6 mm×250 mm)

Mobile phase: A: 0.02% (v/v) phosphoric acid aqueous solution, B: 80% acetonitrile aqueous solution containing 0.02% (v/v) phosphoric acid Linear gradient elution program: 0 min (90:10), 8 min (78:22), 15 min (74:26), 35 min (61:39)

Flow rate: 1 ml/min

Detecting wavelength: 280 nm

Column temperature: 30° C.

The respective retention time of each index ingredient in *Radix salvia miltiorrhira* is: salvianic acid A 5.842 min, protocatechuic aldehyde 9.750 min, salvianolic acid L 17.106 min, salvianolic acid M 18.041 min, salvianolic acid D 20.588 min, rosmarinic acid 24.005 min, salvianolic acid B 27.908 min and salvianolic acid A 31.085 min.

3.3.2 Fingerprint Graph of *Panax notoginseng* and Method for Content Determination 3.3.2.1 Preparation of Test Sample Respectively, 1 g of each sample had been weighted, totally dissolved in 10 ml 4% (v/v) aqueous ammonia by ultrasound and passed through 0.45 um filter membrane. 5 ml of the filtrate was applied on a C18 small column, which was eluted with methanol after being washed with 10 ml water. The obtained eluent was transferred to a 10 ml volumetric flask to be diluted to 10 ml. Two parallel samples were prepared. Injection volume of each sample was 20 ul.

Standard substances of R1, Rg1+Re, Rb1, Rc, Rb2, Rb3, Rd were weighed respectively to prepare the standard solutions. Injection volume of each sample was 20 ul.

3.3.2.2 HPLC Method

Agilent SB-C18 analytical column (4.6 mm×250 mm)
Mobile phase: A: 0.01% (v/v) acetic acid aqueous solution, B: acetonitrile aqueous solution containing 0.01% (v/v) acetic acid.

Linear gradient elution program is shown in the following table.

| time (min) | Phase A | Phase B |
|---|---|---|
| 0 | 80 | 20 |
| 15 | 65 | 35 |
| 25 | 65 | 35 |
| 40 | 57 | 43 |
| 50 | 57 | 43 |
| 65 | 42 | 58 |
| 75 | 25 | 75 |

Flow rate: 0.8 ml/min
Detecting wavelength: 203 nm
Column temperature: 30° C.

The respective retention time of each index ingredient in *Panax notoginseng* is: R1 11.001 min, Rg1+Re 12.252 min, Rb1 20.142 min, Rc 20.877 min, Rb2 22.418 min, Rb3 23.422 min and Rd 25.151 min.

3.3.3 Method for Content Determination of Several Categories Effective Fractions 3.3.3.1 Content of Total Phenolic Acid The protocatechuic aldehyde solution was regarded as the reference solution. Respectively, the solution of 0.3 wt % sodium dodecyl sulfonate and 0.6 wt % potassium ferricyanide and 0.9 wt % ferric chloride solution were added into the reference solution, sample solution and blank solution. By using color reaction, the content of the total phenolic acid had been calculated in accordance with the reference substance comparison method.

3.3.3.2 Content of Total Saponin

Ginsenoside Rg1 solution was regarded as the reference solution, into which 5 wt % vanillin-glacial acetic solution and perchloric acid were added to produce color reaction. Standard curve had been drawn in the light of absorbance of the standard solution with different concentrations. The contents of the total saponin in the samples were calculated by using the standard curve.

3.3.3.3 Content of Total Sugar

The glucose was regarded as the reference solution, into which anthrone reagent was added to produce color reaction. Standard curve had been drawn in the light of absorbance of the standard solution with different concentrations. The contents of the total sugar in the samples were calculated by using the standard curve.

3.3.4 Determination Method for Borneol Content 3.3.4.1 Preparation of Test Sample Naphthalene standard substance was used to prepare the internal standard solution, and borneol and isoborneol standard substances were used to prepare the standard solutions. Injection volume was 1 ul.

0.5 g of dripping pills in the crushed coating was weighed, placed in a 50 ml plastic centrifuge tube and added with 10 ml water. Then, 25 ml ethyl acetate was added to extract by a vigorous shake. The extract liquor was sucked by pipette to be transferred to a 50 ml volumetric flask. According to this method, the solution was re-extracted with ethyl acetate twice and the ethyl acetate used each time was 10 ml. The extract liquors were combined, added with 4 ml internal standard solution and diluted with ethyl acetate to 50 ml. The obtained solution was well shaken to be used as the test solution. Injection volume was 1 ul.

3.3.4.2 Chromatographic Conditions

HP 5% PHME siloxana 30 m (length)×0.25 mm (film thickness) quartz capillary column Column temperature: increased from 60° C. to 135 (150)° C. at a rate of 15° C./min to maintain for 2 min, and the whole procedure lasts 8 min.

Detector: FID (Hydrogen Flame Ionization Detector);
Temperature: 240° C.
Carrier gas: $N_2$
Flow rate: 2.6 ml/min
Temperature in the vaporizer: 200° C.
Number of the theoretical plates calculated by naphthalene was not lower than 10000.
Resolution was larger than 2

3.3.5 Data Statistical Method

Double-tailed paired t-test (software: SPSS13.0) was used to conduct t-test to confirm whether there was significant variation in each index under the test conditions.

Efficiency evaluation model was utilized to evaluate the package, and Data Envelopment Analysis (DEA) had been introduced. The specific model was super-efficiency model by taking different packages as the investigation object. The initial index of different packages was regarded as the input object, and the actual values measured each month as the output object. After being calculated by MYDEA software, the retention efficiency of the ingredients of different packages in each different month was obtained. As a result, the less loss of the ingredients is, the higher the retention efficiency is, and vice versa.

4 Results 4.1 Test Data of Intensive Light Exposure Test 19 index ingredients had been examined in the capsule shell samples with 9 colors on the $0^{th}$, $5^{th}$ and $10^{th}$ day (shown in tables 3-6). Said 19 index ingredients included 8 index ingredients derived from *Radix salvia miltiorrhira* (Table 3), 7 index ingredients derived from *Panax notoginseng* (Table 4), 3 categories effective fractions (total phenolic acid, total saponin and total sugar) (Table 5) and borneol (Table 6).

4.2 Data of Accelerated Stability Test

Respectively, 17 capsule shell samples made of different materials with different colors had been sampled in the $0^{th}$, $1^{st}$, $2^{nd}$, $3^{rd}$, $4.5^{th}$ and $6^{th}$ month. 19 index ingredients had been examined (shown in tables 7-10), and the appearance variation been determined (shown in Table 11).

4.3 Analytical Results of Data 4.3.1 Statistical analytical results of the intensive light exposure test (shown in Table 12)

4.3.2 Statistical analytical results of the accelerated stability test (shown in Table 13)

4.3.3 t-test results between the evaluation results of all indices and the evaluation results of the indices after eliminating those insignificant variation indices in the accelerated stability test (shown in Table 14)

4.3.4 Final assessment results of 17 capsule shells (shown in Table 15)

TABLE 3

Test results of 8 index ingredients of *Radix salvia miltiorrhira* in the samples of capsule shells with 9 different colors

| Code of the capsule shells | salvianic acid A | | | | | protocatechuic aldehyde | | | | |
|---|---|---|---|---|---|---|---|---|---|---|
| | $0^{th}$ day | $5^{th}$ day | variation | $10^{th}$ day | variation | $0^{th}$ day | $5^{th}$ day | variation | $10^{th}$ day | variation |
| MBBB | 9.49 | 8.60 | −0.89 | 8.50 | −0.99 | 3.83 | 4.52 | 0.68 | 4.49 | 0.66 |
| MCB | 9.49 | 8.09 | −1.40 | 8.87 | −0.62 | 3.83 | 4.34 | 0.50 | 4.86 | 1.03 |
| MZB | 9.49 | 8.03 | −1.46 | 10.74 | −1.26 | 3.83 | 4.37 | 0.54 | 4.90 | 1.06 |
| MHB | 9.49 | 8.90 | −0.58 | 9.23 | −0.25 | 3.83 | 4.76 | 0.93 | 4.95 | 1.11 |
| MBHB | 9.49 | 8.86 | −0.62 | 8.66 | −0.83 | 3.83 | 4.23 | 0.39 | 4.61 | 0.77 |
| MHUB | 9.49 | 8.68 | −0.81 | 8.97 | −0.51 | 3.83 | 4.64 | 0.81 | 4.77 | 0.94 |
| MLB | 9.49 | 9.25 | −0.24 | 9.44 | −0.05 | 3.83 | 5.28 | 1.44 | 5.00 | 1.17 |
| MGB | 9.49 | 8.26 | −1.22 | 9.24 | −0.24 | 3.83 | 4.37 | 0.54 | 4.83 | 1.00 |
| MBZBB | 9.49 | 9.55 | 0.06 | 9.45 | −0.03 | 3.83 | 5.16 | 1.33 | 4.94 | 1.11 |

| Code of the capsule shells | salvianolic acid L | | | | | salvianolic acid M | | | | |
|---|---|---|---|---|---|---|---|---|---|---|
| | $0^{th}$ day | $5^{th}$ day | variation | $10^{th}$ day | variation | $0^{th}$ day | $5^{th}$ day | variation | $10^{th}$ day | variation |
| MBBB | 1422 | 3144 | 1722 | 3017 | 1595 | 1625 | 2575 | 950 | 2668 | 1043 |
| MCB | 1422 | 4670 | 3248 | 3750 | 2328 | 1625 | 1932 | 307 | 2905 | 1280 |
| MZB | 1422 | 3054 | 1632 | 4118 | 2696 | 1625 | 2482 | 857 | 4103 | 2478 |
| MHB | 1422 | 3247 | 1825 | 3163 | 1741 | 1625 | 2651 | 1026 | 2953 | 1328 |
| MBHB | 1422 | 2849 | 1427 | 2948 | 1526 | 1625 | 2322 | 697 | 2747 | 1122 |
| MHUB | 1422 | 3311 | 1889 | 3046 | 1624 | 1625 | 4326 | 2701 | 2877 | 1252 |
| MLB | 1422 | 3354 | 1932 | 2989 | 1567 | 1625 | 2733 | 1108 | 2860 | 1235 |
| MGB | 1422 | 3237 | 1815 | 3252 | 1830 | 1625 | 1820 | 195 | 2839 | 1214 |
| MBZBB | 1422 | 3514 | 2092 | 3480 | 2058 | 1625 | 3086 | 1461 | 3090 | 1465 |

| Code of the capsule shells | salvianolic acid D | | | | | rosmarinic acid | | | | |
|---|---|---|---|---|---|---|---|---|---|---|
| | $0^{th}$ day | $5^{th}$ day | variation | $10^{th}$ day | variation | $0^{th}$ day | $5^{th}$ day | variation | $10^{th}$ day | variation |
| MBBB | 1788 | 2758 | 970 | 2797 | 1009 | 1.56 | 1.05 | −0.51 | 1.06 | −0.50 |
| MCB | 1788 | 3058 | 1270 | 2981 | 1193 | 1.56 | 1.04 | −0.52 | 1.22 | −0.34 |
| MZB | 1788 | 2670 | 882 | 5743 | 3955 | 1.56 | 1.04 | −0.52 | 1.26 | −0.30 |
| MHB | 1788 | 2939 | 1151 | 3074 | 1286 | 1.56 | 1.14 | −0.42 | 1.15 | −0.41 |
| MBHB | 1788 | 2644 | 856 | 2858 | 1070 | 1.56 | 1.05 | −0.51 | 1.07 | −0.49 |
| MHUB | 1788 | 2979 | 1191 | 3273 | 1485 | 1.56 | 1.12 | −0.44 | 1.28 | −0.28 |
| MLB | 1788 | 3054 | 1266 | 3085 | 1297 | 1.56 | 1.32 | −0.24 | 1.19 | −0.37 |
| MGB | 1788 | 2567 | 779 | 2980 | 1192 | 1.56 | 1.11 | −0.45 | 1.12 | −0.44 |
| MBZBB | 1788 | 3210 | 1422 | 3045 | 1257 | 1.56 | 1.02 | −0.54 | 1.30 | −0.26 |

| Code of the capsule shells | salvianolic acid B | | | | | salvianolic acid A | | | | |
|---|---|---|---|---|---|---|---|---|---|---|
| | $0^{th}$ day | $5^{th}$ day | variation | $10^{th}$ day | variation | $0^{th}$ day | $5^{th}$ day | variation | $10^{th}$ day | variation |
| MBBB | 1.49 | 2.22 | 0.73 | 2.32 | 0.83 | 2.76 | 0.34 | −2.42 | 1.40 | −1.36 |
| MCB | 1.49 | 2.51 | 1.02 | 3.22 | 1.73 | 3.28 | 0.28 | −3.00 | 2.31 | −0.97 |
| MZB | 1.49 | 2.12 | 0.63 | 3.11 | 1.62 | 3.03 | 0.67 | −2.36 | 2.16 | −0.87 |
| MHB | 1.49 | 2.40 | 0.91 | 2.78 | 1.29 | 3.07 | 0.36 | −2.71 | 2.48 | −0.59 |
| MBHB | 1.49 | 2.07 | 0.58 | 2.40 | 0.91 | 2.68 | 0.38 | −2.30 | 1.77 | −0.91 |
| MHUB | 1.49 | 2.41 | 0.92 | 2.51 | 1.02 | 2.79 | 1.53 | −1.26 | 2.03 | −0.76 |
| MLB | 1.49 | 2.44 | 0.95 | 2.63 | 1.14 | 2.02 | 0.45 | −1.57 | 1.19 | −0.83 |
| MGB | 1.49 | 2.16 | 0.67 | 2.53 | 1.04 | 2.2 | 0.39 | −1.81 | 1.90 | −0.30 |
| MBZBB | 1.49 | 2.93 | 1.44 | 2.90 | 1.41 | 2.07 | 0.45 | −1.62 | 1.81 | −0.26 |

TABLE 4

Test results of 7 index ingredients of *Panax notoginseng* in the samples of capsule shells with 9 different colors

| Code of the capsule shells | R1 | | | | | Rg1 + Re | | | | | Rb1 | | | | |
|---|---|---|---|---|---|---|---|---|---|---|---|---|---|---|---|
| | $0^{th}$ day | $5^{th}$ day | variation | $10^{th}$ day | variation | $0^{th}$ day | $5^{th}$ day | variation | $10^{th}$ day | variation | $0^{th}$ day | $5^{th}$ day | variation | $10^{th}$ day | variation |
| MBBB | 0.95 | 0.56 | −0.39 | 0.70 | −0.25 | 4.02 | 2.60 | −1.42 | 2.96 | −1.06 | 2.29 | 1.34 | −0.94 | 1.50 | −0.78 |
| MCB | 0.95 | 0.48 | −0.47 | 0.65 | −0.30 | 4.02 | 2.18 | −1.84 | 2.73 | −1.28 | 2.29 | 1.11 | −1.17 | 1.36 | −0.93 |
| MZB | 0.95 | 0.61 | −0.34 | 0.60 | −0.36 | 4.02 | 2.75 | −1.26 | 2.64 | −1.37 | 2.29 | 1.52 | −0.76 | 1.41 | −0.88 |
| MHB | 0.95 | 0.61 | −0.34 | 0.60 | −0.35 | 4.02 | 2.72 | −1.30 | 2.78 | −1.23 | 2.29 | 1.46 | −0.82 | 1.46 | −0.82 |

TABLE 4-continued

Test results of 7 index ingredients of *Panax notoginseng* in the samples of capsule shells with 9 different colors

| | | | | | | | | | | | | | | |
|---|---|---|---|---|---|---|---|---|---|---|---|---|---|---|
| MBHB | 0.95 | 0.58 | −0.37 | 0.68 | −0.28 | 4.02 | 2.60 | −1.41 | 2.99 | −1.03 | 2.29 | 1.42 | −0.86 | 1.58 | −0.70 |
| MHUB | 0.95 | 0.58 | −0.37 | 0.74 | −0.21 | 4.02 | 2.42 | −1.60 | 2.83 | −1.18 | 2.29 | 1.29 | −1.00 | 1.53 | −0.75 |
| MLB | 0.95 | 0.67 | −0.28 | 0.65 | −0.30 | 4.02 | 3.02 | −1.00 | 2.78 | −1.23 | 2.29 | 1.54 | −0.74 | 1.51 | −0.77 |
| MGB | 0.95 | 0.65 | −0.30 | 0.59 | −0.37 | 4.02 | 2.81 | −1.21 | 2.64 | −1.38 | 2.29 | 1.50 | −0.79 | 1.34 | −0.95 |
| MBZBB | 0.95 | 0.59 | −0.36 | 0.58 | −0.37 | 4.02 | 2.57 | −1.44 | 2.50 | −1.52 | 2.29 | 1.36 | −0.93 | 1.19 | −1.10 |

| Code of the capsule shells | Rc | | | | | Rb2 | | | | |
|---|---|---|---|---|---|---|---|---|---|---|
| | $0^{th}$ day | $5^{th}$ day | variation | $10^{th}$ day | variation | $0^{th}$ day | $5^{th}$ day | variation | $10^{th}$ day | variation |
| MBBB | 0.20 | 0.11 | −0.09 | 0.16 | −0.04 | 0.48 | 0.19 | −0.29 | 0.10 | −0.38 |
| MCB | 0.20 | 0.12 | −0.09 | 0.11 | −0.09 | 0.48 | 0.13 | −0.35 | 0.15 | −0.34 |
| MZB | 0.20 | 0.17 | −0.03 | 0.16 | −0.04 | 0.48 | 0.27 | −0.21 | 0.19 | −0.29 |
| MHB | 0.20 | 0.20 | 0.00 | 0.14 | −0.06 | 0.48 | 0.29 | −0.20 | 0.10 | −0.38 |
| MBHB | 0.20 | 0.16 | −0.04 | 0.19 | −0.02 | 0.48 | 0.16 | −0.32 | 0.24 | −0.24 |
| MHUB | 0.20 | 0.16 | −0.04 | 0.22 | 0.02 | 0.48 | 0.17 | −0.32 | 0.33 | −0.15 |
| MLB | 0.20 | 0.13 | −0.07 | 0.17 | −0.03 | 0.48 | 0.28 | −0.20 | 0.19 | −0.29 |
| MGB | 0.20 | 0.27 | 0.07 | 0.11 | −0.09 | 0.48 | 0.08 | −0.40 | 0.11 | −0.37 |
| MBZBB | 0.20 | 0.16 | −0.04 | 0.10 | −0.10 | 0.48 | 0.10 | −0.38 | 0.08 | −0.40 |

| Code of the capsule shells | Rb3 | | | | | Rd | | | | |
|---|---|---|---|---|---|---|---|---|---|---|
| | $0^{th}$ day | $5^{th}$ day | variation | $10^{th}$ day | variation | $0^{th}$ day | $5^{th}$ day | variation | $10^{th}$ day | variation |
| MBBB | 0.2432 | 0.17 | −0.08 | 0.20 | −0.04 | 0.1793 | 0.19 | 0.01 | 0.19 | 0.01 |
| MCB | 0.2432 | 0.14 | −0.10 | 0.17 | −0.08 | 0.1793 | 0.24 | 0.06 | 0.17 | −0.01 |
| MZB | 0.2432 | 0.20 | −0.04 | 0.19 | −0.05 | 0.1793 | 0.19 | 0.01 | 0.17 | −0.01 |
| MHB | 0.2432 | 0.21 | −0.03 | 0.20 | −0.04 | 0.1793 | 0.32 | 0.14 | 0.17 | −0.01 |
| MBHB | 0.2432 | 0.20 | −0.05 | 0.21 | −0.03 | 0.1793 | 0.31 | 0.13 | 0.17 | −0.01 |
| MHUB | 0.2432 | 0.19 | −0.06 | 0.22 | −0.02 | 0.1793 | 0.25 | 0.07 | 0.34 | 0.16 |
| MLB | 0.2432 | 0.22 | −0.02 | 0.21 | −0.03 | 0.1793 | 0.25 | 0.07 | 0.33 | 0.15 |
| MGB | 0.2432 | 0.21 | −0.04 | 0.17 | −0.07 | 0.1793 | 0.24 | 0.06 | 0.19 | 0.01 |
| MBZBB | 0.2432 | 0.20 | −0.05 | 0.16 | −0.09 | 0.1793 | 0.18 | 0.00 | 0.29 | 0.11 |

TABLE 5

Test results of index ingredients of 3 categories effective fractions in the samples of capsule shells with 9 different colors

| Code of the capsule shells | total phenolic acid % | | | | | total saponin % | | | | | total sugar % | | | | |
|---|---|---|---|---|---|---|---|---|---|---|---|---|---|---|---|
| | $0^{th}$ day | $5^{th}$ day | variation | $10^{th}$ day | variation | $0^{th}$ day | $5^{th}$ day | variation | $10^{th}$ day | variation | $0^{th}$ day | $5^{th}$ day | variation | $10^{th}$ day | variation |
| MBBB | 1.85 | 1.75 | −0.10 | 1.75 | −0.10 | 4.30 | 4.41 | 0.11 | 4.51 | 0.21 | 0.0142 | 0.0530 | 0.0388 | 0.0532 | 0.0390 |
| MCB | 1.85 | 1.77 | −0.08 | 1.81 | −0.04 | 4.30 | 4.52 | 0.22 | 4.91 | 0.61 | 0.0142 | 0.0534 | 0.0392 | 0.0533 | 0.0391 |
| MZB | 1.85 | 1.84 | −0.01 | 0.18 | −1.67 | 4.30 | 4.86 | 0.56 | 4.39 | 0.09 | 0.0142 | 0.0541 | 0.0399 | 0.0516 | 0.0374 |
| MHB | 1.85 | 1.87 | 0.02 | 0.51 | −1.34 | 4.30 | 4.56 | 0.26 | 4.35 | 0.05 | 0.0142 | 0.0528 | 0.0386 | 0.0531 | 0.0389 |
| MBHB | 1.85 | 1.86 | 0.01 | 0.17 | −1.68 | 4.30 | 5.11 | 0.81 | 4.74 | 0.44 | 0.0142 | 0.0534 | 0.0392 | 0.0504 | 0.0362 |
| MHUB | 1.85 | 1.89 | 0.04 | 0.18 | −1.67 | 4.30 | 5.16 | 0.86 | 4.99 | 0.69 | 0.0142 | 0.0540 | 0.0398 | 0.0534 | 0.0392 |
| MLB | 1.85 | 1.99 | 0.14 | 1.79 | −0.06 | 4.30 | 4.54 | 0.24 | 4.81 | 0.51 | 0.0142 | 0.0544 | 0.0402 | 0.0504 | 0.0362 |
| MGB | 1.85 | 2.01 | 0.16 | 2.10 | 0.25 | 4.30 | 4.56 | 0.26 | 4.79 | 0.49 | 0.0142 | 0.0537 | 0.0395 | 0.0529 | 0.0387 |
| MBZBB | 1.85 | 1.99 | 0.14 | 2.04 | 0.19 | 4.30 | 4.50 | 0.20 | 5.06 | 0.76 | 0.0142 | 0.0538 | 0.0396 | 0.0535 | 0.0393 |

TABLE 6

Test results of borneol content in the samples of capsule shells with 9 different colors

| Code of the capsule shells | Content of borneol | | | | |
|---|---|---|---|---|---|
| | $0^{th}$ day | $5^{th}$ day | variation | $10^{th}$ day | variation |
| MBBB | 15.93 | 16.48 | 0.55 | 16.32 | 0.39 |
| MCB | 15.93 | 15.63 | −0.30 | 15.27 | −0.66 |
| MZB | 15.93 | 16.14 | 0.21 | 15.92 | −0.01 |
| MHB | 15.93 | 16.35 | 0.42 | 16.36 | 0.43 |
| MBHB | 15.93 | 15.46 | −0.47 | 15.39 | −0.54 |
| MHUB | 15.93 | 16.34 | 0.41 | 15.93 | 0.00 |
| MLB | 15.93 | 15.99 | 0.06 | 16.12 | 0.19 |
| MGB | 15.93 | 15.58 | −0.35 | 15.49 | −0.44 |
| MBZBB | 15.93 | 14.15 | −1.78 | 13.83 | −2.10 |

TABLE 7

Test results of 8 index ingredients of *Radix salvia miltiorrhira* in the 17 samples of capsule shells made of different materials with different colors

| Code of the capsule shells | 0th month | 1st month | variation | 2nd month | variation | 3rd month | variation | 4.5th month | variation | 6th month | variation |
|---|---|---|---|---|---|---|---|---|---|---|---|
| salvianic acid A ||||||||||||
| MWB | 19.14 | 11.22 | −7.92 | 9.25 | −9.89 | 14.31 | −4.83 | 18.43 | −0.71 | 9.06 | −10.08 |
| MWS | 20.31 | 10.86 | −9.45 | 9.27 | −11.04 | 14.91 | −5.40 | 18.72 | −1.59 | 8.00 | −12.31 |
| MBBB | 21.08 | 11.29 | −9.79 | 8.73 | −12.35 | 15.13 | −5.95 | 19.28 | −1.80 | 7.87 | −13.21 |
| MBBS | 20.23 | 10.70 | −9.53 | 9.14 | −11.09 | 14.93 | −5.30 | 17.21 | −3.02 | 8.99 | −11.24 |
| ZBBB | 19.63 | 11.39 | −8.24 | 9.67 | −9.96 | 17.60 | −2.03 | 17.16 | −2.47 | 7.21 | −12.42 |
| ZBBS | 19.57 | 11.13 | −8.44 | 9.51 | −10.06 | 15.62 | −3.95 | 18.72 | −0.85 | 9.41 | −10.16 |
| CB | 20.04 | 11.18 | −8.86 | 9.37 | −10.67 | 15.46 | −4.58 | 17.04 | −3.00 | 7.02 | −13.02 |
| CS | 18.47 | 11.11 | −7.36 | 9.81 | −8.66 | 15.48 | −2.99 | 17.85 | −0.62 | 9.13 | −9.34 |
| MCB | 19.00 | 11.20 | −7.80 | 9.54 | −9.46 | 17.47 | −1.53 | 17.77 | −1.23 | 7.92 | −11.08 |
| MCS | 20.71 | 11.38 | −9.33 | 10.46 | −10.25 | 15.39 | −5.32 | 16.20 | −4.51 | 10.96 | −9.75 |
| MZB | 18.76 | 11.03 | −7.73 | 9.53 | −9.23 | 15.47 | −3.29 | 19.03 | 0.27 | 8.06 | −10.70 |
| MHB | 18.84 | 11.16 | −7.68 | 9.51 | −9.33 | 16.50 | −2.34 | 23.28 | 4.44 | 9.41 | −9.43 |
| MHUB | 18.56 | 11.10 | −7.46 | 9.65 | −8.91 | 16.24 | −2.32 | 21.41 | 2.85 | 9.85 | −8.71 |
| MBHB | 18.76 | 11.14 | −7.62 | 9.71 | −9.05 | 15.29 | −3.47 | 19.14 | 0.38 | 8.54 | −10.22 |
| MLB | 18.37 | 11.12 | −7.25 | 9.85 | −8.52 | 16.06 | −2.31 | 17.11 | −1.26 | 9.49 | −8.88 |
| MGB | 18.86 | 11.59 | −7.27 | 9.97 | −8.89 | 14.76 | −4.10 | 18.60 | −0.26 | 8.99 | −9.87 |
| MBZBB | 18.39 | 10.83 | −7.56 | 9.72 | −8.67 | 16.14 | −2.25 | 19.07 | 0.68 | 8.04 | −10.35 |
| protocatechuic aldehyde ||||||||||||
| MWB | 5.07 | 3.46 | −1.61 | 3.88 | −1.19 | 3.50 | −1.57 | 4.26 | −0.81 | 4.18 | −0.89 |
| MWS | 5.41 | 3.73 | −1.68 | 4.11 | −1.3 | 3.83 | −1.58 | 4.09 | −1.32 | 4.39 | −1.02 |
| MBBB | 5.29 | 3.44 | −1.85 | 3.62 | −1.67 | 3.66 | −1.63 | 4.43 | −0.86 | 3.45 | −1.84 |
| MBBS | 5.45 | 3.67 | −1.78 | 4.17 | −1.28 | 4.21 | −1.24 | 4.49 | −0.96 | 4.56 | −0.89 |
| ZBBB | 5.2 | 3.58 | −1.62 | 4.17 | −1.03 | 5.13 | −0.07 | 3.70 | −1.50 | 3.41 | −1.79 |
| ZBBS | 5.17 | 3.75 | −1.42 | 4.25 | −0.92 | 4.01 | −1.16 | 4.31 | −0.86 | 4.28 | −0.89 |
| CB | 5.23 | 3.48 | −1.75 | 3.87 | −1.36 | 3.79 | −1.44 | 3.70 | −1.53 | 3.01 | −2.22 |
| CS | 4.99 | 3.71 | −1.28 | 4.2 | −0.79 | 3.73 | −1.26 | 4.13 | −0.86 | 4.37 | −0.62 |
| MCB | 4.32 | 3.54 | −0.78 | 4.02 | −0.3 | 4.70 | 0.38 | 4.06 | −0.26 | 4.26 | −0.06 |
| MCS | 5.39 | 3.92 | −1.47 | 5.03 | −0.36 | 4.43 | −0.96 | 3.82 | −1.57 | 4.92 | −0.47 |
| MZB | 4.97 | 3.49 | −1.48 | 4.05 | −0.92 | 3.85 | −1.12 | 4.31 | −0.66 | 3.59 | −1.38 |
| MHB | 5 | 3.54 | −1.46 | 4.13 | −0.87 | 4.35 | −0.65 | 5.57 | 0.57 | 4.42 | −0.58 |
| MHUB | 4.91 | 3.56 | −1.35 | 4.21 | −0.7 | 4.02 | −0.89 | 4.84 | −0.07 | 4.48 | −0.43 |
| MBHB | 4.94 | 3.6 | −1.34 | 4.22 | −0.72 | 3.82 | −1.12 | 4.24 | −0.70 | 3.68 | −1.26 |
| MLB | 4.86 | 3.64 | −1.22 | 4.41 | −0.45 | 4.04 | −0.82 | 3.80 | −1.06 | 4.57 | −0.29 |
| MGB | 5.02 | 3.7 | −1.32 | 4.32 | −0.7 | 3.50 | −1.52 | 4.22 | −0.80 | 4.19 | −0.83 |
| MBZBB | 4.83 | 3.51 | −1.32 | 4.18 | −0.65 | 4.09 | −0.74 | 4.14 | −0.69 | 2.83 | −2.00 |
| salvianolic acid L ||||||||||||
| MWB | 1668 | 1377 | −291 | 1292 | −376 | 1105 | −563 | 1254 | −414 | 1079 | −589 |
| MWS | 1791 | 1476 | −315 | 1375 | −416 | 1237 | −554 | 1328 | −463 | 1170 | −621 |
| MBBB | 1763 | 1427 | −336 | 1225 | −538 | 1162 | −601 | 1376 | −387 | 884 | −879 |
| MBBS | 1807 | 1463 | −344 | 1375 | −432 | 1310 | −497 | 1391 | −416 | 1205 | −602 |
| ZBBB | 1742 | 1467 | −275 | 1414 | −328 | 1536 | −206 | 1136 | −606 | 901 | −841 |
| ZBBS | 1731 | 1535 | −196 | 1405 | −326 | 1279 | −452 | 1353 | −378 | 1223 | −508 |
| CB | 1694 | 1412 | −282 | 1351 | −343 | 1260 | −434 | 1218 | −476 | 911 | −783 |
| CS | 1663 | 1530 | −133 | 1474 | −189 | 1280 | −383 | 1148 | −515 | 1172 | −491 |
| MCB | 1669 | 1427 | −242 | 1333 | −336 | 1559 | −110 | 1274 | −395 | 1081 | −588 |
| MCS | 1859 | 1589 | −270 | 1722 | −137 | 1477 | −382 | 1263 | −596 | 1258 | −601 |
| MZB | 1685 | 1410 | −275 | 1355 | −330 | 1240 | −445 | 1415 | −270 | 951 | −734 |
| MHB | 1673 | 1435 | −238 | 1354 | −319 | 1481 | −192 | 1815 | 142 | 1328 | −345 |
| MHUB | 1619 | 1430 | −189 | 1422 | −197 | 1315 | −304 | 1507 | −112 | 1216 | −403 |
| MBHB | 1688 | 1453 | −235 | 1443 | −245 | 1192 | −496 | 1257 | −431 | 1030 | −658 |
| MLB | 1638 | 1453 | −185 | 1487 | −151 | 1304 | −334 | 1255 | −383 | 1212 | −426 |
| MGB | 1691 | 1487 | −204 | 1415 | −276 | 1064 | −627 | 1315 | −376 | 1118 | −573 |
| MBZBB | 1636 | 1408 | −228 | 1396 | −240 | 1299 | −337 | 1294 | −342 | 927 | −709 |
| salvianolic acid M ||||||||||||
| MWB | 1615 | 1344 | −271 | 1200 | −415 | 1023 | −592 | 1197 | −418 | 1045 | −570 |
| MWS | 1705 | 1448 | −257 | 1271 | −434 | 1152 | −553 | 1228 | −477 | 1140 | −565 |
| MBBB | 1656 | 1395 | −261 | 1156 | −500 | 1115 | −541 | 1313 | −343 | 857 | −799 |
| MBBS | 1712 | 1490 | −222 | 1300 | −412 | 1241 | −471 | 1332 | −380 | 1165 | −547 |
| ZBBB | 1620 | 1495 | −125 | 1331 | −289 | 1409 | −211 | 1060 | −560 | 851 | −769 |
| ZBBS | 1610 | 1555 | −55 | 1336 | −274 | 1207 | −403 | 1256 | −354 | 1159 | −451 |
| CB | 1545 | 1455 | −90 | 1274 | −271 | 1181 | −364 | 1140 | −405 | 828 | −717 |
| CS | 1559 | 1526 | −33 | 1397 | −162 | 1195 | −364 | 1085 | −474 | 1132 | −427 |
| MCB | 1598 | 1422 | −176 | 1328 | −270 | 1505 | −93 | 1221 | −377 | 1071 | −527 |
| MCS | 1773 | 1570 | −203 | 1664 | −109 | 1383 | −390 | 1169 | −604 | 1231 | −542 |
| MZB | 1604 | 1397 | −207 | 1336 | −268 | 1138 | −466 | 1378 | −226 | 888 | −716 |
| MHB | 1591 | 1393 | −198 | 1345 | −246 | 1389 | −202 | 1741 | 150 | 1780 | 189 |
| MHUB | 1516 | 1396 | −120 | 1413 | −103 | 1220 | −296 | 1329 | −187 | 1115 | −401 |
| MBHB | 1579 | 1393 | −186 | 1434 | −145 | 1072 | −507 | 1185 | −394 | 939 | −640 |

TABLE 7-continued

Test results of 8 index ingredients of *Radix salvia miltiorrhira* in the 17 samples of capsule shells made of different materials with different colors

| Code of the capsule shells | $0^{th}$ month | $1^{st}$ month | variation | $2^{nd}$ month | variation | $3^{rd}$ month | variation | $4.5^{th}$ month | variation | $6^{th}$ month | variation |
|---|---|---|---|---|---|---|---|---|---|---|---|
| MLB | 1515 | 1400 | −115 | 1470 | −45 | 1193 | −322 | 1107 | −408 | 1399 | −116 |
| MGB | 1558 | 1426 | −132 | 1374 | −184 | 991 | −567 | 1186 | −372 | 1019 | −539 |
| MBZBB | 1477 | 1354 | −123 | 1342 | −135 | 1177 | −300 | 1146 | −331 | 864 | −613 |
| | | | | | salvianolic acid D | | | | | | |
| MWB | 1788 | 1326 | −462 | 1030 | −758 | 730 | −1058 | 744 | −1044 | 502 | −1286 |
| MWS | 1894 | 1444 | −450 | 1119 | −775 | 830 | −1064 | 769 | −1125 | 616 | −1278 |
| MBBB | 1871 | 1363 | −508 | 1023 | −848 | 856 | −1015 | 883 | −988 | 412 | −1459 |
| MBBS | 1917 | 1375 | −542 | 1117 | −800 | 890 | −1027 | 854 | −1063 | 556 | −1361 |
| ZBBB | 1860 | 1365 | −495 | 1085 | −775 | 985 | −875 | 584 | −1276 | 985 | −875 |
| ZBBS | 1827 | 1398 | −429 | 1081 | −746 | 812 | −1015 | 683 | −1144 | 474 | −1353 |
| CB | 1830 | 1308 | −522 | 1028 | −802 | 794 | −1036 | 612 | −1218 | 342 | −1488 |
| CS | 1754 | 1380 | −374 | 1092 | −662 | 816 | −938 | 632 | −1122 | 502 | −1252 |
| MCB | 1622 | 1342 | −280 | 1067 | −555 | 1118 | −504 | 798 | −824 | 511 | −1111 |
| MCS | 1889 | 1525 | −364 | 1394 | −495 | 1050 | −839 | 687 | −1202 | 618 | −1271 |
| MZB | 1750 | 1314 | −436 | 1074 | −676 | 804 | −946 | 890 | −860 | 421 | −1329 |
| MHB | 1757 | 1328 | −429 | 1085 | −672 | 1037 | −720 | 1109 | −648 | 848 | −909 |
| MHUB | 1712 | 1338 | −374 | 1183 | −529 | 959 | −753 | 694 | −1018 | 607 | −1105 |
| MBHB | 1743 | 1339 | −404 | 1198 | −545 | 768 | −975 | 810 | −933 | 428 | −1315 |
| MLB | 1703 | 1329 | −374 | 1663 | −40 | 871 | −832 | 729 | −974 | 639 | −1064 |
| MGB | 1752 | 1364 | −388 | 1099 | −653 | 787 | −965 | 720 | −1032 | 505 | −1247 |
| MBZBB | 1689 | 1282 | −407 | 1070 | −619 | 863 | −826 | 697 | −992 | 452 | −1237 |
| | | | | | rosmarinic acid | | | | | | |
| MWB | 1.98 | 1.39 | −0.59 | 1.29 | −0.69 | 1.19 | −0.79 | 1.42 | −0.56 | 0.83 | −1.15 |
| MWS | 2 | 1.47 | −0.53 | 1.36 | −0.64 | 1.31 | −0.69 | 1.52 | −0.48 | 0.89 | −1.11 |
| MBBB | 1.95 | 1.43 | −0.52 | 1.21 | −0.74 | 1.22 | −0.73 | 1.55 | −0.4 | 0.69 | −1.26 |
| MBBS | 1.99 | 1.45 | −0.54 | 1.36 | −0.63 | 1.39 | −0.6 | 1.55 | −0.44 | 0.93 | −1.06 |
| ZBBB | 1.92 | 1.44 | −0.48 | 1.4 | −0.52 | 1.59 | −0.33 | 1.27 | −0.65 | 0.71 | −1.21 |
| ZBBS | 1.91 | 1.49 | −0.42 | 1.39 | −0.52 | 1.33 | −0.58 | 1.5 | −0.41 | 0.91 | −1 |
| CB | 1.84 | 1.41 | −0.43 | 1.34 | −0.5 | 1.32 | −0.52 | 1.37 | −0.47 | 0.75 | −1.09 |
| CS | 1.84 | 1.5 | −0.34 | 1.44 | −0.4 | 1.35 | −0.49 | 1.3 | −0.54 | 0.9 | −0.94 |
| MCB | 1.91 | 1.42 | −0.49 | 1.36 | −0.55 | 1.62 | −0.29 | 1.4 | −0.51 | 1.03 | −0.88 |
| MCS | 2.06 | 1.57 | −0.49 | 1.69 | −0.37 | 1.52 | −0.54 | 1.42 | −0.64 | 0.95 | −1.11 |
| MZB | 1.86 | 1.39 | −0.47 | 1.37 | −0.49 | 1.27 | −0.59 | 1.51 | −0.35 | 0.72 | −1.14 |
| MHB | 1.89 | 1.41 | −0.48 | 1.38 | −0.51 | 1.51 | −0.38 | 1.96 | 0.07 | 1.08 | −0.81 |
| MHUB | 1.84 | 1.41 | −0.43 | 1.43 | −0.41 | 1.37 | −0.47 | 1.71 | −0.13 | 0.9 | −0.94 |
| MBHB | 1.84 | 1.43 | −0.41 | 1.46 | −0.38 | 1.26 | −0.58 | 1.45 | −0.39 | 0.78 | −1.06 |
| MLB | 1.82 | 1.44 | −0.38 | 1.5 | −0.32 | 1.46 | −0.36 | 1.36 | −0.46 | 0.91 | −0.91 |
| MGB | 1.89 | 1.46 | −0.43 | 1.43 | −0.46 | 1.21 | −0.68 | 1.47 | −0.42 | 0.76 | −1.13 |
| MBZBB | 1.82 | 1.39 | −0.43 | 1.4 | −0.42 | 1.57 | −0.25 | 1.44 | −0.38 | 0.68 | −1.14 |
| | | | | | salvianolic acid B | | | | | | |
| MWB | 3.14 | 1.28 | −1.86 | 1.76 | −1.38 | 1.37 | −1.77 | 1.18 | −1.96 | 0.42 | −2.72 |
| MWS | 3.26 | 1.35 | −1.91 | 1.91 | −1.35 | 1.51 | −1.75 | 1.25 | −2.01 | 0.46 | −2.8 |
| MBBB | 3.17 | 1.28 | −1.89 | 1.64 | −1.53 | 1.39 | −1.78 | 1.28 | −1.89 | 0.31 | −2.86 |
| MBBS | 3.21 | 1.3 | −1.91 | 1.83 | −1.38 | 1.53 | −1.68 | 1.28 | −1.93 | 0.44 | −2.77 |
| ZBBB | 2.99 | 1.28 | −1.71 | 1.9 | −1.09 | 1.81 | −1.18 | 1.02 | −1.97 | 0.72 | −2.27 |
| ZBBS | 2.95 | 1.33 | −1.62 | 1.87 | −1.08 | 1.47 | −1.48 | 1.18 | −1.77 | 0.44 | −2.51 |
| CB | 2.85 | 1.25 | −1.6 | 1.79 | −1.06 | 1.45 | −1.4 | 1.07 | −1.78 | 0.4 | −2.45 |
| CS | 2.85 | 1.32 | −1.53 | 1.89 | −0.96 | 1.48 | −1.37 | 1.01 | −1.84 | 0.42 | −2.43 |
| MCB | 2.79 | 1.27 | −1.52 | 1.79 | −1 | 1.98 | −0.81 | 1.14 | −1.65 | 0.41 | −2.38 |
| MCS | 3.07 | 1.42 | −1.65 | 2.42 | −0.65 | 1.84 | −1.23 | 1.11 | −1.96 | 0.48 | −2.59 |
| MZB | 2.88 | 1.24 | −1.64 | 1.82 | −1.06 | 1.43 | −1.45 | 1.27 | −1.61 | 0.34 | −2.54 |
| MHB | 2.85 | 1.26 | −1.59 | 1.81 | −1.04 | 1.84 | −1.01 | 1.77 | −1.08 | 0.49 | −2.36 |
| MHUB | 2.78 | 1.25 | −1.53 | 1.91 | −0.87 | 1.59 | −1.19 | 1.4 | −1.38 | 0.46 | −2.32 |
| MBHB | 3.06 | 1.25 | −1.81 | 1.93 | −1.13 | 1.34 | −1.72 | 1.2 | −1.86 | 0.4 | −2.66 |
| MLB | 2.82 | 1.25 | −1.57 | 1.98 | −0.84 | 1.48 | −1.34 | 1.14 | −1.68 | 0.48 | −2.34 |
| MGB | 2.95 | 1.29 | −1.66 | 1.86 | −1.09 | 1.25 | −1.7 | 1.16 | −1.79 | 0.64 | −2.31 |
| MBZBB | 2.79 | 1.22 | −1.57 | 1.83 | −0.96 | 1.46 | −1.33 | 1.34 | −1.45 | 0.42 | −2.37 |
| | | | | | salvianolic acid A | | | | | | |
| MWB | 3.02 | 2.29 | −0.73 | 1.9 | −1.12 | 1.82 | −1.2 | 1.89 | −1.13 | 1.97 | −1.05 |
| MWS | 3.28 | 2.47 | −0.81 | 1.98 | −1.3 | 2.04 | −1.24 | 1.8 | −1.48 | 2.24 | −1.04 |
| MBBB | 3.03 | 2.36 | −0.67 | 1.71 | −1.32 | 2 | −1.03 | 2.08 | −0.95 | 1.58 | −1.45 |
| MBBS | 3.07 | 2.36 | −0.71 | 1.9 | −1.17 | 2.23 | −0.84 | 2.22 | −0.85 | 2.2 | −0.87 |
| ZBBB | 2.68 | 2.24 | −0.44 | 1.85 | −0.83 | 2.53 | −0.15 | 1.61 | −1.07 | 1.15 | −1.53 |
| ZBBS | 2.79 | 2.42 | −0.37 | 1.94 | −0.85 | 2.05 | −0.74 | 1.89 | −0.9 | 1.92 | −0.87 |
| CB | 2.02 | 2.23 | 0.21 | 1.71 | −0.31 | 1.88 | −0.14 | 1.54 | −0.48 | 1.15 | −0.87 |
| CS | 2.2 | 2.37 | 0.17 | 1.95 | −0.25 | 1.83 | −0.37 | 1.57 | −0.63 | 1.99 | −0.21 |
| MCB | 2.07 | 2.24 | 0.17 | 2.2 | 0.13 | 2.42 | 0.35 | 1.66 | −0.41 | 1.89 | −0.18 |
| MCS | 2.42 | 2.49 | 0.07 | 2.24 | −0.18 | 2.16 | −0.26 | 1.59 | −0.83 | 2.1 | −0.32 |
| MZB | 2.16 | 2.12 | −0.04 | 2.1 | −0.06 | 1.67 | −0.49 | 2.02 | −0.14 | 1.5 | −0.66 |

TABLE 7-continued

Test results of 8 index ingredients of *Radix salvia miltiorrhira* in the 17 samples of capsule shells made of different materials with different colors

| Code of the capsule shells | $0^{th}$ month | $1^{st}$ month | variation | $2^{nd}$ month | variation | $3^{rd}$ month | variation | $4.5^{th}$ month | variation | $6^{th}$, month | variation |
|---|---|---|---|---|---|---|---|---|---|---|---|
| MHB | 1.42 | 2.1 | 0.68 | 2.18 | 0.76 | 1.97 | 0.55 | 2.68 | 1.26 | 1.94 | 0.52 |
| MHUB | 1.21 | 2.11 | 0.9 | 2.23 | 1.02 | 1.58 | 0.37 | 2.07 | 0.86 | 1.86 | 0.65 |
| MBHB | 1.58 | 2.07 | 0.49 | 2.33 | 0.75 | 1.39 | −0.19 | 1.84 | 0.26 | 1.32 | −0.26 |
| MLB | 1.41 | 2.01 | 0.6 | 2.38 | 0.97 | 1.44 | 0.03 | 1.53 | 0.12 | 1.78 | 0.37 |
| MGB | 1.24 | 1.97 | 0.73 | 2.26 | 1.02 | 1.34 | 0.1 | 1.73 | 0.49 | 1.74 | 0.5 |
| MBZBB | 1.28 | 2.01 | 0.73 | 2.08 | 0.8 | 1.62 | 0.34 | 1.42 | 0.14 | 1.11 | −0.17 |

TABLE 8

Test results of 7 index ingredients of *Panax notoginseng* in the 17 samples of capsule shells made of different materials with different colors

| Code of the capsule shells | $0^{th}$ month | $1^{st}$ month | variation | $2^{nd}$ month | variation | $3^{rd}$ month | variation | $4.5^{th}$ month | variation | $6^{th}$ month | variation |
|---|---|---|---|---|---|---|---|---|---|---|---|
| R1 | | | | | | | | | | | |
| MWB | 0.48 | 0.73 | 0.25 | 0.79 | 0.31 | 0.47 | −0.01 | 0.47 | −0.01 | 0.69 | 0.21 |
| MWS | 0.6 | 0.77 | 0.17 | 0.96 | 0.36 | 0.53 | −0.07 | 0.5 | −0.1 | 0.85 | 0.25 |
| MBBB | 0.49 | 0.75 | 0.26 | 0.87 | 0.38 | 0.47 | −0.02 | 0.44 | −0.05 | 0.76 | 0.27 |
| MBBS | 0.57 | 0.83 | 0.26 | 0.84 | 0.27 | 0.54 | −0.03 | 0.54 | −0.03 | 0.57 | 0 |
| ZBBB | 0.48 | 0.79 | 0.31 | 0.77 | 0.29 | 0.47 | −0.01 | 0.43 | −0.05 | 0.67 | 0.19 |
| ZBBS | 0.55 | 0.88 | 0.33 | 0.84 | 0.29 | 0.53 | −0.02 | 0.53 | −0.02 | 0.8 | 0.25 |
| CB | 0.48 | 0.77 | 0.29 | 0.8 | 0.32 | 0.46 | −0.02 | 0.48 | 0 | 0.67 | 0.19 |
| CS | 0.53 | 0.9 | 0.37 | 0.96 | 0.43 | 0.54 | 0.01 | 0.64 | 0.11 | 0.81 | 0.28 |
| MCB | 0.59 | 0.74 | 0.15 | 0.89 | 0.3 | 0.43 | −0.16 | 0.52 | −0.07 | 0.67 | 0.08 |
| MCS | 0.48 | 0.86 | 0.38 | 0.94 | 0.46 | 0.56 | 0.08 | 0.58 | 0.1 | 0.67 | 0.19 |
| MZB | 0.46 | 0.77 | 0.31 | 0.75 | 0.29 | 0.44 | −0.02 | 0.57 | 0.11 | 0.69 | 0.23 |
| MHB | 0.48 | 0.79 | 0.31 | 0.82 | 0.34 | 0.46 | −0.02 | 0.45 | −0.03 | 0.68 | 0.2 |
| MHUB | 0.48 | 0.73 | 0.25 | 0.77 | 0.29 | 0.44 | −0.04 | 0.4 | −0.08 | 0.62 | 0.14 |
| MBHB | 0.55 | 0.75 | 0.2 | 0.83 | 0.28 | 0.47 | −0.08 | 0.48 | −0.07 | 0.64 | 0.09 |
| MLB | 0.54 | 0.74 | 0.2 | 0.85 | 0.31 | 0.47 | −0.07 | 0.44 | −0.1 | 0.64 | 0.1 |
| MGB | 0.46 | 0.74 | 0.28 | 0.66 | 0.2 | 0.5 | 0.04 | 0.46 | 0 | 0.72 | 0.26 |
| MBZBB | 0.49 | 0.76 | 0.27 | 0.67 | 0.18 | 0.51 | 0.02 | 0.48 | −0.01 | 0.71 | 0.22 |
| Rg1 + Re | | | | | | | | | | | |
| MWB | 2.34 | 3.94 | 1.6 | 3.87 | 1.53 | 2.32 | −0.02 | 2.23 | −0.11 | 3.23 | 0.89 |
| MWS | 2.79 | 4.22 | 1.43 | 4.45 | 1.66 | 2.68 | −0.11 | 2.45 | −0.34 | 3.85 | 1.06 |
| MBBB | 2.31 | 3.99 | 1.68 | 4.27 | 1.96 | 2.35 | 0.04 | 2.15 | −0.16 | 3.43 | 1.12 |
| MBBS | 2.71 | 4.22 | 1.51 | 4.48 | 1.77 | 2.68 | −0.03 | 2.68 | −0.03 | 2.76 | 0.05 |
| ZBBB | 2.31 | 4.1 | 1.79 | 3.94 | 1.63 | 2.28 | −0.03 | 2.18 | −0.13 | 3.11 | 0.8 |
| ZBBS | 2.57 | 4.5 | 1.93 | 4.42 | 1.85 | 2.68 | 0.11 | 2.5 | −0.07 | 3.63 | 1.06 |
| CB | 2.29 | 4.03 | 1.74 | 4.27 | 1.98 | 2.31 | 0.02 | 2.17 | −0.12 | 3.11 | 0.82 |
| CS | 2.47 | 4.48 | 2.01 | 4.73 | 2.26 | 2.64 | 0.17 | 2.72 | 0.25 | 3.73 | 1.26 |
| MCB | 2.86 | 3.94 | 1.08 | 4.3 | 1.44 | 2.24 | −0.62 | 2.35 | −0.51 | 3.18 | 0.32 |
| MCS | 2.34 | 4.49 | 2.15 | 4.55 | 2.21 | 2.72 | 0.38 | 2.63 | 0.29 | 3.15 | 0.81 |
| MZB | 2.28 | 4.09 | 1.81 | 3.99 | 1.71 | 2.18 | −0.1 | 2.54 | 0.26 | 3.04 | 0.76 |
| MHB | 2.39 | 4.11 | 1.72 | 4.2 | 1.81 | 2.25 | −0.14 | 2.19 | −0.2 | 3.01 | 0.62 |
| MHUB | 2.43 | 3.83 | 1.4 | 4.05 | 1.62 | 2.22 | −0.21 | 2.02 | −0.41 | 2.92 | 0.49 |
| MBHB | 2.32 | 3.9 | 1.58 | 4.16 | 1.84 | 2.4 | 0.08 | 2.15 | −0.17 | 3 | 0.68 |
| MLB | 2.33 | 3.79 | 1.46 | 4.3 | 1.97 | 2.39 | 0.06 | 2.2 | −0.13 | 2.86 | 0.53 |
| MGB | 2.23 | 3.84 | 1.61 | 3.31 | 1.08 | 2.32 | 0.09 | 2.3 | 0.07 | 3.25 | 1.02 |
| MBZBB | 2.41 | 3.93 | 1.52 | 3.41 | 1 | 2.28 | −0.13 | 2.3 | −0.11 | 3.19 | 0.78 |
| Rb1 | | | | | | | | | | | |
| MWB | 1.69 | 2.27 | 0.58 | 1.91 | 0.22 | 1.61 | −0.08 | 1.73 | 0.04 | 1.81 | 0.12 |
| MWS | 2.04 | 2.38 | 0.34 | 2.15 | 0.11 | 1.97 | −0.07 | 1.93 | −0.11 | 2.26 | 0.22 |
| MBBB | 1.63 | 2.51 | 0.88 | 2.17 | 0.54 | 1.7 | 0.07 | 1.65 | 0.02 | 1.96 | 0.33 |
| MBBS | 1.97 | 2.57 | 0.6 | 2.24 | 0.27 | 1.93 | −0.04 | 2.13 | 0.16 | 1.68 | −0.29 |
| ZBBB | 1.61 | 2.37 | 0.76 | 1.98 | 0.37 | 1.6 | −0.01 | 1.66 | 0.05 | 1.77 | 0.16 |
| ZBBS | 1.85 | 2.57 | 0.72 | 2.26 | 0.41 | 1.93 | 0.08 | 2.01 | 0.16 | 2.15 | 0.3 |
| CB | 1.61 | 2.37 | 0.76 | 2.24 | 0.63 | 1.68 | 0.07 | 1.64 | 0.03 | 1.75 | 0.14 |
| CS | 1.76 | 2.77 | 1.01 | 2.29 | 0.53 | 1.98 | 0.22 | 2.21 | 0.45 | 2.24 | 0.48 |
| MCB | 2.11 | 2.18 | 0.07 | 2.07 | −0.04 | 1.64 | −0.47 | 1.77 | −0.34 | 1.87 | −0.24 |
| MCS | 1.64 | 2.73 | 1.09 | 2.2 | 0.56 | 1.98 | 0.34 | 2.02 | 0.38 | 1.82 | 0.18 |
| MZB | 1.64 | 2.48 | 0.84 | 2.02 | 0.38 | 1.49 | −0.15 | 1.89 | 0.25 | 1.74 | 0.1 |
| MHB | 1.73 | 2.52 | 0.79 | 1.99 | 0.26 | 1.6 | −0.13 | 1.48 | −0.25 | 1.74 | 0.01 |
| MHUB | 1.7 | 2.47 | 0.77 | 2.01 | 0.31 | 1.61 | −0.09 | 1.36 | −0.34 | 1.65 | −0.05 |
| MBHB | 1.58 | 2.32 | 0.74 | 1.94 | 0.36 | 1.84 | 0.26 | 1.35 | −0.23 | 1.68 | 0.1 |

TABLE 8-continued

Test results of 7 index ingredients of *Panax notoginseng* in the 17 samples of capsule shells made of different materials with different colors

| Code of the capsule shells | 0th month | 1st month | var-iation | 2nd month | var-iation | 3rd month | var-iation | 4.5th month | var-iation | 6th month | var-iation |
|---|---|---|---|---|---|---|---|---|---|---|---|
| MLB | 1.68 | 2.25 | 0.57 | 1.99 | 0.31 | 1.95 | 0.27 | 1.5 | −0.18 | 1.62 | −0.06 |
| MGB | 1.57 | 2.3 | 0.73 | 1.55 | −0.02 | 1.79 | 0.22 | 1.55 | −0.02 | 1.89 | 0.32 |
| MBZBB | 1.74 | 2.34 | 0.6 | 1.6 | −0.14 | 1.71 | −0.03 | 1.55 | −0.19 | 1.87 | 0.13 |
| Rc | | | | | | | | | | | |
| MWB | 0.17 | 0.22 | 0.05 | 0.22 | 0.05 | 0.17 | 0 | 0.35 | 0.18 | 0.17 | 0 |
| MWS | 0.21 | 0.4 | 0.19 | 0.19 | −0.02 | 0.17 | −0.04 | 0.25 | 0.04 | 0.21 | 0 |
| MBBB | 0.16 | 0.51 | 0.35 | 0.32 | 0.16 | 0.16 | 0 | 0.25 | 0.09 | 0.22 | 0.06 |
| MBBS | 0.2 | 0.33 | 0.13 | 0.25 | 0.05 | 0.17 | −0.03 | 0.25 | 0.05 | 0.16 | −0.04 |
| ZBBB | 0.16 | 0.33 | 0.17 | 0.31 | 0.15 | 0.15 | −0.01 | 0.14 | −0.02 | 0.22 | 0.06 |
| ZBBS | 0.18 | 0.35 | 0.17 | 0.32 | 0.14 | 0.17 | −0.01 | 0.27 | 0.09 | 0.21 | 0.03 |
| CB | 0.15 | 0.35 | 0.2 | 0.39 | 0.24 | 0.28 | 0.13 | 0.24 | 0.09 | 0.17 | 0.02 |
| CS | 0.17 | 0.56 | 0.39 | 0.27 | 0.1 | 0.19 | 0.02 | 0.5 | 0.33 | 0.27 | 0.1 |
| MCB | 0.19 | 0.22 | 0.03 | 0.21 | 0.02 | 0.17 | −0.02 | 0.24 | 0.05 | 0.18 | −0.01 |
| MCS | 0.16 | 0.37 | 0.21 | 0.21 | 0.05 | 0.18 | 0.02 | 0.33 | 0.17 | 0.23 | 0.07 |
| MZB | 0.16 | 0.47 | 0.31 | 0.2 | 0.04 | 0.13 | −0.03 | 0.26 | 0.1 | 0.19 | 0.03 |
| MHB | 0.17 | 0.49 | 0.32 | 0.21 | 0.04 | 0.16 | −0.01 | 0.11 | −0.06 | 0.22 | 0.05 |
| MHUB | 0.17 | 0.6 | 0.43 | 0.21 | 0.04 | 0.14 | −0.03 | 0.13 | −0.04 | 0.18 | 0.01 |
| MBHB | 0.14 | 0.24 | 0.1 | 0.21 | 0.07 | 0.24 | 0.1 | 0.12 | −0.02 | 0.16 | 0.02 |
| MLB | 0.2 | 0.33 | 0.13 | 0.2 | 0 | 0.24 | 0.04 | 0.11 | −0.09 | 0.17 | −0.03 |
| MGB | 0.14 | 0.32 | 0.18 | 0.17 | 0.03 | 0.21 | 0.07 | 0.12 | −0.02 | 0.24 | 0.1 |
| MBZBB | 0.15 | 0.28 | 0.13 | 0.17 | 0.02 | 0.24 | 0.09 | 0.13 | −0.02 | 0.24 | 0.09 |
| Rb2 | | | | | | | | | | | |
| MWB | 0.19 | 0.65 | 0.46 | 0.12 | −0.07 | 0.33 | 0.14 | 0.3 | 0.11 | 0.05 | −0.14 |
| MWS | 0.16 | 0.86 | 0.7 | 0.12 | −0.04 | 0.37 | 0.21 | 0.35 | 0.19 | 0.08 | −0.08 |
| MBBB | 0.15 | 0.69 | 0.54 | 0.11 | −0.04 | 0.27 | 0.12 | 0.24 | 0.09 | 0.07 | −0.08 |
| MBBS | 0.11 | 0.69 | 0.58 | 0.1 | −0.01 | 0.27 | 0.16 | 0.24 | 0.13 | 0.09 | −0.02 |
| ZBBB | 0.1 | 0.65 | 0.55 | 0.12 | 0.02 | 0.13 | 0.03 | 0.24 | 0.14 | 0.07 | −0.03 |
| ZBBS | 0.08 | 0.72 | 0.64 | 0.12 | 0.04 | 0.16 | 0.08 | 0.17 | 0.09 | 0.07 | −0.01 |
| CB | 0.11 | 0.65 | 0.54 | 0.16 | 0.05 | 0.67 | 0.56 | 0.13 | 0.02 | 0.06 | −0.05 |
| CS | 0.11 | 0.8 | 0.69 | 0.11 | 0 | 0.54 | 0.43 | 0.39 | 0.28 | 0.12 | 0.01 |
| MCB | 0.11 | 0.52 | 0.41 | 0.09 | −0.02 | 0.44 | 0.33 | 0.21 | 0.1 | 0.08 | −0.03 |
| MCS | 0.08 | 0.54 | 0.46 | 0.1 | 0.02 | 0.38 | 0.3 | 0.24 | 0.16 | 0.08 | 0 |
| MZB | 0.18 | 0.49 | 0.31 | 0.31 | 0.13 | 0.27 | 0.09 | 0.13 | −0.05 | 0.07 | −0.11 |
| MHB | 0.2 | 0.56 | 0.36 | 0.11 | −0.09 | 0.25 | 0.05 | 0.11 | −0.09 | 0.08 | −0.12 |
| MHUB | 0.09 | 0.52 | 0.43 | 0.07 | −0.02 | 0.31 | 0.22 | 0.3 | 0.21 | 0.06 | −0.03 |
| MBHB | 0.07 | 0.51 | 0.44 | 0.12 | 0.05 | 0.35 | 0.28 | 0.25 | 0.18 | 0.05 | −0.02 |
| MLB | 0.25 | 0.49 | 0.24 | 0.1 | −0.15 | 0.32 | 0.07 | 0.3 | 0.05 | 0.06 | −0.19 |
| MGB | 0.25 | 0.4 | 0.15 | 0.07 | −0.18 | 0.24 | −0.01 | 0.3 | 0.05 | 0.08 | −0.17 |
| MBZBB | 0.23 | 0.44 | 0.21 | 0.06 | −0.17 | 0.19 | −0.04 | 0.26 | 0.03 | 0.09 | −0.14 |
| Rb3 | | | | | | | | | | | |
| MWB | 0.21 | 0.21 | 0 | 0.2 | −0.01 | 0.19 | −0.02 | 0.23 | 0.02 | 0.23 | 0.02 |
| MWS | 0.24 | 0.26 | 0.02 | 0.24 | 0 | 0.24 | 0 | 0.23 | −0.01 | 0.29 | 0.05 |
| MBBB | 0.21 | 0.27 | 0.06 | 0.24 | 0.03 | 0.23 | 0.02 | 0.19 | −0.02 | 0.25 | 0.04 |
| MBBS | 0.26 | 0.24 | −0.02 | 0.25 | −0.01 | 0.23 | −0.03 | 0.25 | −0.01 | 0.2 | −0.06 |
| ZBBB | 0.21 | 0.23 | 0.02 | 0.22 | 0.01 | 0.2 | −0.01 | 0.19 | −0.02 | 0.24 | 0.03 |
| ZBBS | 0.23 | 0.27 | 0.04 | 0.3 | 0.07 | 0.24 | 0.01 | 0.23 | 0 | 0.27 | 0.04 |
| CB | 0.21 | 0.25 | 0.04 | 0.26 | 0.05 | 0.31 | 0.1 | 0.19 | −0.02 | 0.22 | 0.01 |
| CS | 0.22 | 0.3 | 0.08 | 0.26 | 0.04 | 0.23 | 0.01 | 0.3 | 0.08 | 0.34 | 0.12 |
| MCB | 0.26 | 0.22 | −0.04 | 0.24 | −0.02 | 0.19 | −0.07 | 0.23 | −0.03 | 0.25 | −0.01 |
| MCS | 0.21 | 0.26 | 0.05 | 0.25 | 0.04 | 0.25 | 0.04 | 0.26 | 0.05 | 0.23 | 0.02 |
| MZB | 0.21 | 0.26 | 0.05 | 0.21 | 0 | 0.22 | 0.01 | 0.24 | 0.03 | 0.23 | 0.02 |
| MHB | 0.22 | 0.26 | 0.04 | 0.22 | 0 | 0.23 | 0.01 | 0.26 | 0.04 | 0.23 | 0.01 |
| MHUB | 0.22 | 0.23 | 0.01 | 0.21 | −0.01 | 0.2 | −0.02 | 0.26 | 0.04 | 0.21 | −0.01 |
| MBHB | 0.22 | 0.22 | 0 | 0.22 | 0 | 0.2 | −0.02 | 0.25 | 0.03 | 0.21 | −0.01 |
| MLB | 0.23 | 0.23 | 0 | 0.23 | 0 | 0.21 | −0.02 | 0.25 | 0.02 | 0.21 | −0.02 |
| MGB | 0.2 | 0.23 | 0.03 | 0.18 | −0.02 | 0.19 | −0.01 | 0.27 | 0.07 | 0.25 | 0.05 |
| MBZBB | 0.21 | 0.23 | 0.02 | 0.19 | −0.02 | 0.19 | −0.02 | 0.26 | 0.05 | 0.26 | 0.05 |
| Rd | | | | | | | | | | | |
| MWB | 0.42 | 0.27 | −0.15 | 0.25 | −0.17 | 0.24 | −0.18 | 0.6 | 0.18 | 0.42 | 0 |
| MWS | 0.35 | 0.25 | −0.1 | 0.3 | −0.05 | 0.42 | 0.07 | 0.59 | 0.24 | 0.51 | 0.16 |
| MBBB | 0.2 | 0.28 | 0.08 | 0.27 | 0.07 | 0.31 | 0.11 | 0.55 | 0.35 | 0.44 | 0.24 |
| MBBS | 0.27 | 0.31 | 0.04 | 0.32 | 0.05 | 0.36 | 0.09 | 0.66 | 0.39 | 0.49 | 0.22 |
| ZBBB | 0.2 | 0.29 | 0.09 | 0.26 | 0.06 | 0.29 | 0.09 | 0.75 | 0.55 | 0.4 | 0.2 |
| ZBBS | 0.23 | 0.31 | 0.08 | 0.32 | 0.09 | 0.34 | 0.11 | 0.71 | 0.48 | 0.48 | 0.25 |
| CB | 0.47 | 0.28 | −0.19 | 0.28 | −0.19 | 0.38 | −0.09 | 0.69 | 0.22 | 0.39 | −0.08 |
| CS | 0.53 | 0.32 | −0.21 | 0.33 | −0.2 | 0.36 | −0.17 | 0.69 | 0.16 | 0.51 | −0.02 |
| MCB | 0.41 | 0.28 | −0.13 | 0.29 | −0.12 | 0.28 | −0.13 | 0.69 | 0.28 | 0.42 | 0.01 |
| MCS | 0.25 | 0.31 | 0.06 | 0.33 | 0.08 | 0.37 | 0.12 | 0.68 | 0.43 | 0.39 | 0.14 |
| MZB | 0.21 | 0.27 | 0.06 | 0.26 | 0.05 | 0.29 | 0.08 | 0.69 | 0.48 | 0.36 | 0.15 |

TABLE 8-continued

Test results of 7 index ingredients of *Panax notoginseng* in the 17 samples of capsule shells made of different materials with different colors

| Code of the capsule shells | $0^{th}$ month | $1^{st}$ month | variation | $2^{nd}$ month | variation | $3^{rd}$ month | variation | $4.5^{th}$ month | variation | $6^{th}$ month | variation |
|---|---|---|---|---|---|---|---|---|---|---|---|
| MHB   | 0.22 | 0.28 | 0.06  | 0.27 | 0.05  | 0.3  | 0.08  | 0.2  | −0.02 | 0.36 | 0.14  |
| MHUB  | 0.48 | 0.26 | −0.22 | 0.25 | −0.23 | 0.29 | −0.19 | 0.17 | −0.31 | 0.33 | −0.15 |
| MBHB  | 0.44 | 0.27 | −0.17 | 0.27 | −0.17 | 0.46 | 0.02  | 0.17 | −0.27 | 0.35 | −0.09 |
| MLB   | 0.48 | 0.26 | −0.22 | 0.28 | −0.2  | 0.55 | 0.07  | 0.2  | −0.28 | 0.34 | −0.14 |
| MGB   | 0.4  | 0.27 | −0.13 | 0.23 | −0.17 | 0.56 | 0.16  | 0.19 | −0.21 | 0.39 | −0.01 |
| MBZBB | 0.37 | 0.28 | −0.09 | 0.3  | −0.07 | 0.52 | 0.15  | 0.19 | −0.18 | 0.38 | 0.01  |

TABLE 9

Test data of 3 index ingredients of the effective fractions in the 17 samples of capsule shells with different colors

| Code of the capsule shells | $0^{th}$ month | $1^{st}$ month | variation | $2^{nd}$ month | variation | $3^{rd}$ month | variation | $4.5^{th}$ month | variation | $6^{th}$ month | variation |
|---|---|---|---|---|---|---|---|---|---|---|---|
| total phenolic acid % | | | | | | | | | | | |
| MWB   | 1.937 | 1.908 | −0.030 | 2.191 | 0.254 | 1.953 | 0.016  | 1.930 | −0.008 | 1.762 | −0.175 |
| MWS   | 1.816 | 1.752 | −0.064 | 2.431 | 0.615 | 1.754 | −0.062 | 1.983 | 0.167  | 1.944 | 0.129  |
| MBBB  | 1.707 | 1.726 | 0.019  | 1.858 | 0.151 | 1.768 | 0.061  | 1.934 | 0.227  | 1.760 | 0.053  |
| MBBS  | 1.845 | 1.648 | −0.197 | 2.219 | 0.373 | 1.924 | 0.079  | 1.892 | 0.047  | 1.903 | 0.058  |
| ZBBB  | 1.775 | 1.787 | 0.012  | 2.006 | 0.231 | 1.864 | 0.090  | 1.914 | 0.139  | 1.831 | 0.056  |
| ZBBS  | 1.818 | 1.704 | −0.114 | 2.208 | 0.390 | 1.757 | −0.061 | 1.788 | −0.031 | 1.850 | 0.032  |
| CB    | 1.880 | 1.560 | −0.320 | 2.597 | 0.717 | 1.935 | 0.055  | 1.850 | −0.030 | 1.751 | −0.129 |
| CS    | 1.654 | 1.820 | 0.166  | 3.019 | 1.365 | 2.102 | 0.448  | 1.839 | 0.185  | 1.863 | 0.209  |
| MCB   | 1.810 | 1.660 | −0.150 | 2.170 | 0.360 | 1.753 | −0.057 | 1.779 | −0.030 | 1.838 | 0.029  |
| MCS   | 1.704 | 1.650 | −0.054 | 2.998 | 1.294 | 1.752 | 0.048  | 1.805 | 0.101  | 1.837 | 0.133  |
| MZB   | 1.753 | 1.378 | −0.375 | 2.561 | 0.807 | 1.966 | 0.213  | 1.704 | −0.050 | 1.879 | 0.125  |
| MHB   | 1.805 | 1.976 | 0.171  | 2.753 | 0.948 | 1.744 | −0.060 | 1.938 | 0.133  | 1.872 | 0.067  |
| MHUB  | 1.746 | 1.345 | −0.401 | 2.602 | 0.856 | 1.917 | 0.171  | 1.989 | 0.244  | 1.806 | 0.060  |
| MBHB  | 1.827 | 1.919 | 0.092  | 2.597 | 0.769 | 2.023 | 0.195  | 1.585 | −0.243 | 1.698 | −0.129 |
| MLB   | 1.798 | 1.353 | −0.445 | 2.557 | 0.759 | 1.864 | 0.066  | 1.737 | −0.060 | 1.857 | 0.059  |
| MGB   | 1.684 | 1.857 | 0.173  | 2.412 | 0.728 | 2.108 | 0.424  | 1.787 | 0.103  | 1.916 | 0.232  |
| MBZBB | 1.812 | 1.536 | −0.276 | 2.710 | 0.898 | 1.842 | 0.030  | 1.907 | 0.095  | 2.045 | 0.234  |
| total saponin % | | | | | | | | | | | |
| MWB   | 4.656 | 6.579 | 1.924 | 3.915 | −0.740 | 4.879 | 0.224  | 4.593 | −0.063 | 4.538 | −0.117 |
| MWS   | 3.867 | 7.264 | 3.397 | 3.969 | 0.102  | 4.634 | 0.767  | 4.643 | 0.776  | 4.832 | 0.965  |
| MBBB  | 4.082 | 6.789 | 2.707 | 3.780 | −0.303 | 4.685 | 0.603  | 4.551 | 0.469  | 4.633 | 0.551  |
| MBBS  | 3.795 | 7.248 | 3.453 | 5.109 | 1.314  | 5.028 | 1.233  | 4.984 | 1.189  | 4.925 | 1.130  |
| ZBBB  | 3.893 | 6.488 | 2.595 | 3.502 | −0.391 | 4.771 | 0.878  | 4.500 | 0.607  | 5.148 | 1.254  |
| ZBBS  | 4.009 | 7.028 | 3.019 | 4.035 | 0.026  | 5.062 | 1.053  | 5.034 | 1.025  | 4.336 | 0.327  |
| CB    | 4.039 | 6.459 | 2.421 | 5.576 | 1.537  | 5.566 | 1.527  | 4.889 | 0.851  | 4.757 | 0.718  |
| CS    | 3.944 | 7.077 | 3.133 | 8.999 | 5.055  | 6.210 | 2.266  | 5.118 | 1.174  | 4.753 | 0.809  |
| MCB   | 4.540 | 6.561 | 2.021 | 4.274 | −0.265 | 5.186 | 0.646  | 5.035 | 0.496  | 5.056 | 0.517  |
| MCS   | 3.907 | 7.037 | 3.130 | 6.058 | 2.151  | 5.436 | 1.530  | 5.096 | 1.189  | 5.142 | 1.235  |
| MZB   | 4.375 | 6.620 | 2.244 | 4.791 | 0.416  | 5.651 | 1.276  | 5.071 | 0.696  | 5.214 | 0.839  |
| MHB   | 4.246 | 8.770 | 4.525 | 7.108 | 2.862  | 5.257 | 1.011  | 5.071 | 0.825  | 5.074 | 0.829  |
| MHUB  | 3.881 | 6.997 | 3.116 | 5.813 | 1.932  | 5.354 | 1.472  | 5.177 | 1.296  | 4.772 | 0.891  |
| MBHB  | 4.464 | 6.469 | 2.005 | 5.185 | 0.721  | 5.513 | 1.049  | 5.237 | 0.773  | 5.015 | 0.551  |
| MLB   | 4.459 | 6.444 | 1.984 | 5.839 | 1.380  | 6.423 | 1.963  | 5.715 | 1.256  | 5.084 | 0.625  |
| MGB   | 4.345 | 6.061 | 1.717 | 7.675 | 3.331  | 5.138 | 0.794  | 5.052 | 0.707  | 4.996 | 0.651  |
| MBZBB | 3.884 | 7.066 | 3.182 | 7.258 | 3.374  | 4.976 | 1.091  | 5.016 | 1.132  | 5.156 | 1.272  |
| total sugar % | | | | | | | | | | | |
| MWB   | 0.016 | 0.013 | −0.003 | 0.040 | 0.023 | 0.049 | 0.033 | 0.054 | 0.037 | 0.055 | 0.039 |
| MWS   | 0.016 | 0.018 | 0.002  | 0.038 | 0.023 | 0.045 | 0.029 | 0.052 | 0.036 | 0.054 | 0.038 |
| MBBB  | 0.015 | 0.015 | 0.000  | 0.038 | 0.023 | 0.041 | 0.026 | 0.045 | 0.030 | 0.051 | 0.036 |
| MBBS  | 0.015 | 0.017 | 0.002  | 0.034 | 0.019 | 0.039 | 0.024 | 0.050 | 0.035 | 0.054 | 0.039 |
| ZBBB  | 0.016 | 0.015 | −0.001 | 0.032 | 0.016 | 0.039 | 0.023 | 0.052 | 0.036 | 0.053 | 0.037 |
| ZBBS  | 0.015 | 0.017 | 0.002  | 0.037 | 0.022 | 0.040 | 0.025 | 0.046 | 0.031 | 0.053 | 0.037 |
| CB    | 0.015 | 0.015 | 0.000  | 0.042 | 0.027 | 0.047 | 0.031 | 0.052 | 0.037 | 0.055 | 0.040 |
| CS    | 0.015 | 0.019 | 0.004  | 0.040 | 0.025 | 0.041 | 0.026 | 0.056 | 0.041 | 0.055 | 0.040 |
| MCB   | 0.015 | 0.016 | 0.001  | 0.040 | 0.025 | 0.041 | 0.026 | 0.052 | 0.037 | 0.053 | 0.038 |
| MCS   | 0.015 | 0.017 | 0.002  | 0.036 | 0.021 | 0.041 | 0.026 | 0.051 | 0.035 | 0.054 | 0.038 |
| MZB   | 0.016 | 0.014 | −0.001 | 0.037 | 0.021 | 0.043 | 0.028 | 0.049 | 0.034 | 0.052 | 0.036 |
| MHB   | 0.015 | 0.019 | 0.004  | 0.040 | 0.025 | 0.039 | 0.024 | 0.048 | 0.033 | 0.053 | 0.038 |
| MHUB  | 0.016 | 0.015 | −0.001 | 0.038 | 0.022 | 0.042 | 0.027 | 0.052 | 0.036 | 0.052 | 0.037 |
| MBHB  | 0.016 | 0.013 | −0.003 | 0.039 | 0.023 | 0.041 | 0.025 | 0.052 | 0.036 | 0.052 | 0.036 |
| MLB   | 0.016 | 0.015 | 0.000  | 0.037 | 0.022 | 0.045 | 0.029 | 0.051 | 0.035 | 0.053 | 0.038 |

TABLE 9-continued

Test data of 3 index ingredients of the effective fractions in the 17 samples of capsule shells with different colors

| Code of the capsule shells | $0^{th}$ month | $1^{st}$ month | variation | $2^{nd}$ month | variation | $3^{rd}$ month | variation | $4.5^{th}$ month | variation | $6^{th}$ month | variation |
|---|---|---|---|---|---|---|---|---|---|---|---|
| MGB | 0.015 | 0.017 | 0.002 | 0.034 | 0.019 | 0.043 | 0.028 | 0.054 | 0.039 | 0.052 | 0.037 |
| MBZBB | 0.016 | 0.016 | 0.000 | 0.045 | 0.029 | 0.043 | 0.027 | 0.053 | 0.037 | 0.051 | 0.035 |

TABLE 10

Test data of borneol content in the 17 samples of capsule shells with different colors

| Code of the capsule shells | $0^{th}$ month | $1^{st}$ month | variation | $2^{nd}$ month | variation | $3^{rd}$ month | variation | $4.5^{th}$ month | variation | $6^{th}$ month | variation |
|---|---|---|---|---|---|---|---|---|---|---|---|
| MWB | 16.29 | 16.01 | -0.28 | 16.16 | -0.13 | 16.47 | 0.18 | 16.66 | 0.37 | 12.11 | -4.18 |
| MWS | 16.54 | 16.78 | 0.24 | 16.08 | -0.46 | 16.87 | 0.33 | 16.90 | 0.36 | 14.18 | -2.36 |
| MBBB | 15.69 | 16.83 | 1.13 | 15.52 | -0.18 | 14.90 | -0.79 | 16.63 | 0.94 | 10.17 | -5.52 |
| MBBS | 15.93 | 17.58 | 1.66 | 15.63 | -0.30 | 16.24 | 0.31 | 16.02 | 0.09 | 14.63 | -1.30 |
| ZBBB | 15.70 | 16.46 | 0.76 | 15.63 | -0.06 | 16.55 | 0.85 | 16.78 | 1.08 | 12.82 | -2.87 |
| ZBBS | 15.79 | 16.22 | 0.43 | 15.72 | -0.07 | 17.07 | 1.28 | 16.00 | 0.21 | 13.01 | -2.78 |
| CB | 15.83 | 15.44 | -0.39 | 15.33 | -0.49 | 15.69 | -0.14 | 16.23 | 0.40 | 14.83 | -1.00 |
| CS | 15.93 | 18.24 | 2.31 | 15.65 | -0.28 | 16.83 | 0.90 | 17.14 | 1.21 | 13.52 | -2.41 |
| MCB | 15.67 | 16.57 | 0.90 | 15.38 | -0.29 | 16.93 | 1.26 | 16.43 | 0.76 | 11.24 | -4.44 |
| MCS | 16.08 | 17.48 | 1.40 | 15.68 | -0.40 | 16.19 | 0.11 | 15.86 | -0.22 | 16.64 | 0.56 |
| MZB | 15.58 | 15.60 | 0.02 | 15.31 | -0.27 | 16.57 | 0.99 | 17.03 | 1.45 | 11.01 | -4.57 |
| MHB | 16.03 | 15.88 | -0.14 | 15.71 | -0.32 | 15.65 | -0.38 | 15.58 | -0.45 | 11.25 | -4.77 |
| MHUB | 15.84 | 14.16 | -1.69 | 15.72 | -0.12 | 16.96 | 1.11 | 16.91 | 1.06 | 12.63 | -3.22 |
| MBHB | 16.01 | 16.20 | 0.19 | 15.46 | -0.55 | 17.05 | 1.04 | 16.44 | 0.44 | 14.88 | -1.13 |
| MLB | 16.24 | 16.52 | 0.28 | 15.58 | -0.66 | 15.84 | -0.40 | 16.17 | -0.07 | 12.89 | -3.35 |
| MGB | 16.08 | 16.55 | 0.47 | 15.64 | -0.44 | 16.29 | 0.21 | 17.06 | 0.98 | 14.07 | -2.01 |
| MBZBB | 15.73 | 16.30 | 0.57 | 15.58 | -0.15 | 16.56 | 0.83 | 15.93 | 0.20 | 13.32 | -2.41 |

TABLE 11

Appearance variation of the capsule shells with different materials in the accelerated stability test

| Sample type | $0^{th}$ month capsule shell appearance | Content character | $1^{th}$ month capsule shell appearance | Content character | $2^{th}$ month capsule shell appearance | Content character | $3^{th}$ month capsule shell appearance | Content character |
|---|---|---|---|---|---|---|---|---|
| MBBB | Standard capsule shell | Standard dripping pill | No significant change | No significant change | dehydration | some dripping pills stick together | become sticky and hard, loss of elasticity, some shells appear erosion of the contents | Dripping pills start to be sticky |
| MBBS | Standard capsule shell | Standard dripping pill | No significant change | No significant change | dehydration | some dripping pills stick together | become sticky and hard, loss of elasticity, some shells appear erosion of the contents | Dripping pills start to be sticky |
| MHUB | Standard capsule shell | Standard dripping pill | No significant change | No significant change | dehydration | some dripping pills stick together | become sticky and hard, loss of elasticity, some shells appear erosion of the contents | Dripping pills start to be sticky |
| MGB | Standard capsule shell | Standard dripping pill | No significant change | No significant change | dehydration | some dripping pills stick together | become sticky and hard, loss of elasticity, some shells appear erosion of the contents | Dripping pills start to be sticky |

TABLE 11-continued

Appearance variation of the capsule shells with different materials in the accelerated stability test

| | | | | | | | | |
|---|---|---|---|---|---|---|---|---|
| ZBBB | Standard capsule shell | Standard dripping pill | No significant change | No significant change | No significant change | No significant change | No significant change | No significant change |
| ZBBS | Standard capsule shell | Standard dripping pill | No significant change | No significant change | No significant change | No significant change | No significant change | No significant change |

| | | 4.5$^{th}$ month | | 6$^{th}$ month | |
|---|---|---|---|---|---|
| | Sample type | capsule shell appearance | Content character | capsule shell appearance | Content character |
| | MBBB | more serious dehydration, more serious erosion, some shells become seriously sticky, and caps of the shell cannot be separated | dripping pills stick into a column and cannot be separated intactly from each other | dehydration and deformation, some form hard block, serious erosion | dripping pills stick into a column, softly stick as a whole and cannot be separated one by one |
| | MBBS | more serious dehydration, more serious erosion, some shells become seriously sticky, and caps of the shell cannot be separated | dripping pills stick into a column and cannot be separated intactly from each other | dehydration and deformation, some form hard block, serious erosion | dripping pills stick into a column, softly stick as a whole and cannot be separated one by one |
| | MHUB | more serious dehydration, more serious erosion, some shells become seriously sticky, and caps of the shell cannot be separated | dripping pills stick into a column and cannot be separated intactly from each other | dehydration and deformation, some form hard block, serious erosion | dripping pills stick into a column, softly stick as a whole and cannot be separated one by one |
| | MGB | more serious dehydration, more serious erosion, some shells become seriously sticky, and caps of the shell cannot be separated | dripping pills stick into a column and cannot be separated intactly from each other | dehydration and deformation, some form hard block, serious erosion | dripping pills stick into a column, softly stick as a whole and cannot be separated one by one |
| | ZBBB | slight dehydration | No significant change | some shells appear slight erosion but the shells are still elastic | no significant change in the appearance of the dripping pills |
| | ZBBS | slight dehydration | No significant change | some shells appear slight erosion but the shells are still elastic | no significant change in the appearance of the dripping pills |

TABLE 12

Statistical results of the test data of the samples of capsule shells with different colors in the intensive light exposure test

| | significant indices | | all indices | | | significant indices | | all indices | |
|---|---|---|---|---|---|---|---|---|---|
| capsule color | capsule code | score | capsule color | capsule code | score | capsule color | capsule code | score | capsule color | capsule code | score |

| capsule color | capsule code | score | capsule color | capsule code | score |
|---|---|---|---|---|---|
| sorting of CCR-I for 5 days | | | | | |
| yellow | MHUB | 2.4641138 | yellow | MHUB | 2.4641138 |
| blue | MLB | 1.6512504 | green | MGB | 1.903328 |
| orange | MCB | 1.3923229 | blue | MLB | 1.6512504 |
| red | MHB | 1.1832373 | orange | MCB | 1.3923229 |
| rubylith (purple) | MBHB | 1.0732775 | red | MHB | 1.2512533 |
| brown | MZB | 1.0595455 | rubylith (purple) | MBHB | 1.0732775 |
| green | MGB | 0.9725099 | brown | MZB | 1.0600987 |
| non-transparent white | MBBB | 0.9326656 | non-transparent white | MBBB | 1.0109615 |
| sorting of CCR-I for 10 days | | | | | |
| brown | MZB | 1.7547322 | brown | MZB | 1.7547322 |
| yellow | MHUB | 1.401499 | yellow | MHUB | 1.5094458 |
| blue | MLB | 1.3260946 | blue | MLB | 1.3867348 |

TABLE 12-continued

Statistical results of the test data of the samples of capsule shells with different colors in the intensive light exposure test

| | significant indices | | all indices | |
|---|---|---|---|---|
| capsule color | capsule code | score | capsule color | capsule code | score |
| green | MGB | 1.1930523 | green | MGB | 1.1930523 |
| red | MHB | 1.1234442 | red | MHB | 1.1234442 |
| orange | MCB | 1.0666818 | orange | MCB | 1.0666818 |
| rubylith (purple) | MBHB | 1.0416402 | rubylith (purple) | MBHB | 1.0416402 |
| non-transparent white | MBBB | 1.0091647 | non-transparent white | MBBB | 1.0300917 |

TABLE 14 t-test results between the evaluation results of all indices and the evaluation results of the indices after eliminating those insignificant variation indices in the accelerated stability test

| Pairing of Table 13A and Table 13B | | t | df | Signal (double-tailed) |
|---|---|---|---|---|
| Pairing 1 | $1^{st}$ month | −2.280 | 16 | 0.037 |
| Pairing 2 | $2^{nd}$ month | −1.995 | 16 | 0.063 |
| Pairing 3 | $3^{rd}$ month | −6.034 | 16 | 0.000 |
| Pairing 4 | $4.5^{th}$ month | −2.012 | 16 | 0.061 |
| Pairing 5 | $6^{th}$ month | −2.046 | 16 | 0.058 |

TABLE 13

Statistical results of the test data of the capsule shells made of different materials with different colors in the accelerated stability test A DEA assessment results of all indices

| Package | $1^{st}$ month | $2^{nd}$ month | $3^{rd}$ month | $4.5^{th}$ month | $6^{th}$ month |
|---|---|---|---|---|---|
| MWB | 1.053 | 1.039 | 1.091 | 1.48 | 1.044 |
| MWS | 1.173 | 1.049 | 1.066 | 1.413 | 1.147 |
| MBBB | 1.259 | 1.157 | 1.128 | 1.125 | 1.11 |
| MBBS | 1.07 | 1.042 | 1.076 | 1.172 | 1.15 |
| ZBBB | 1.137 | 1.141 | 1.412 | 1.107 | 1.788 |
| ZBBS | 1.337 | 1.38 | 1.115 | 1.079 | 1.292 |
| CB | 1.051 | 1.538 | 1.532 | 1.153 | 1.076 |
| CS | 1.27 | 1.511 | 1.21 | 1.281 | 1.545 |
| MCB | 1.155 | 1.158 | 1.382 | 1.184 | 1.238 |
| MCS | 1.198 | 1.436 | 1.439 | 1.282 | 1.375 |
| MZB | 1.038 | 2.724 | 1.153 | 1.222 | 1.062 |
| MHB | 1.673 | 1.487 | 1.495 | 1.121 | 2.042 |
| MHUB | 1.778 | 1.296 | 1.394 | 1.724 | 1.484 |
| MBHB | 1.521 | 1.393 | 1.662 | 1.204 | 1.211 |
| MLB | 1.019 | 1.404 | 1.22 | 1.234 | 1.063 |
| MGB | 1.173 | 1.179 | 1.22 | 1.259 | 1.511 |
| MBZBB | 1.092 | 1.253 | 1.264 | 1.772 | 1.177 |

B DEA assessment results and sorting after eliminating insignificant indices

| Package | $1^{st}$ month | sorting | $2^{nd}$ month | sorting | $3^{rd}$ month | sorting | $4.5^{th}$ month | sorting | $6^{th}$ month | sorting |
|---|---|---|---|---|---|---|---|---|---|---|
| MWB | 1.015 | 16 | 1.034 | 17 | 0.958 | 16 | 1.026 | 16 | 1.044 | 16 |
| MWS | 1.173 | 7 | 1.037 | 15 | 1.005 | 13 | 1.08 | 10 | 1.135 | 11 |
| MBBB | 1.259 | 4 | 1.157 | 7 | 0.923 | 17 | 1.053 | 14 | 1.014 | 17 |
| MBBS | 1.06 | 12 | 1.042 | 14 | 1.006 | 12 | 1.118 | 8 | 1.062 | 14 |
| ZBBB | 1.109 | 10 | 1.122 | 11 | 1.2 | 6 | 1.03 | 15 | 1.562 | 1 |
| ZBBS | 1.337 | 1 | 1.157 | 7 | 1.053 | 10 | 1.076 | 11 | 1.198 | 9 |
| CB | 1.044 | 13 | 1.355 | 2 | 1.252 | 4 | 1.006 | 17 | 1.076 | 12 |
| CS | 1.255 | 5 | 1.355 | 2 | 1.209 | 5 | 1.637 | 1 | 1.54 | 2 |
| MCB | 1.146 | 8 | 1.13 | 9 | 1.358 | 1 | 1.138 | 5 | 1.236 | 7 |
| MCS | 1.198 | 6 | 1.326 | 5 | 1.254 | 3 | 1.12 | 7 | 1.318 | 6 |
| MZB | 1.038 | 14 | 1.036 | 16 | 1 | 15 | 1.055 | 13 | 1.053 | 15 |
| MHB | 1.318 | 2 | 1.333 | 4 | 1.035 | 11 | 1.39 | 2 | 1.479 | 5 |
| MHUB | 1.31 | 3 | 1.047 | 13 | 1.078 | 9 | 1.247 | 4 | 1.484 | 4 |
| MBHB | 1.119 | 9 | 1.091 | 12 | 1.318 | 2 | 1.347 | 3 | 1.211 | 8 |
| MLB | 1.011 | 17 | 1.396 | 1 | 1.088 | 7 | 1.117 | 9 | 1.063 | 13 |
| MGB | 1.107 | 11 | 1.127 | 10 | 1.004 | 14 | 1.124 | 6 | 1.511 | 3 |
| MBZBB | 1.029 | 15 | 1.172 | 6 | 1.08 | 8 | 1.061 | 12 | 1.144 | 10 |

TABLE 15

Final assessment results of 17 kinds of the capsule shells (data from the statistical data of the last 2 columns in Table 13B)

| package | ZBBB | CS | MGB | MHUB | MHB | MCS | MCB | MBHB | ZBBS |
|---|---|---|---|---|---|---|---|---|---|
| 6th month | 1.562 | 1.54 | 1.511 | 1.484 | 1.479 | 1.318 | 1.236 | 1.211 | 1.198 |
| sorting | 1 | 2 | 3 | 4 | 5 | 6 | 7 | 8 | 9 |

| package | MBZBB | MWS | CB | MLB | MBBS | MZB | MWB | MBBB |
|---|---|---|---|---|---|---|---|---|
| 6th month | 1.144 | 1.135 | 1.076 | 1.063 | 1.062 | 1.053 | 1.044 | 1.014 |
| sorting | 10 | 11 | 12 | 13 | 14 | 15 | 16 | 17 |

5 Conclusions 5.1 Preferred Material of the Capsule Shell

As revealed in the results of the aforesaid accelerated stability, compared with the gelatin capsule shell, the plant-derived capsule shell showed a better protective effect in view of the variation of capsule's content appearance and the ingredient concentration.

5.2 Preferred Color of the Capsule Shell

From the statistical results of the test data obtained in the intensive light exposure test (Table 12), the intensive light exert effect on all components of CSDP, and different color capsule shells showed different protective effects. However, any of colored capsule shells can bring about protective effect on the content, and the non-transparent white ranked the last place in both the cases of the significant index evaluation and all indices evaluation. Different colored capsule shells can be ranked on the basis of the test data. Overall, the preferred color of the capsule shell is orange, yellow, green and blue with the corresponding wavelength in a range of 446-620 nm. In particular, the color of the capsule shell is as follows: the orange with a corresponding wavelength at 592-620 nm, the blue at 446-500 nm, the yellow at 577-592 nm and the green at 500-577 nm. Wherein, the yellow (at 577-592 nm) and the green (at 500-577 nm) capsule shells capable of scattering visible light of medium-wavelength (500-592 nm) offer the most effective protection for the CSDP.

5.3 Selection Basis for Long-Term Stability Test

According to the final statistical results of the accelerated stability test (Table 15), the conclusion can be drawn as follows:

(1) In terms of the material, the plant-derived capsule shell is better than the gelatin.
(2) In terms of color, the preferred color of the capsule shell is orange, yellow, green and blue with a corresponding wavelength in a range of 446-620 nm. More preferably, the color is the yellow (at 577-592 nm) and the green (at 500-577 nm).
(3) After consideration of the aforesaid two aspects, the shell of CSDP capsule is preferred to be selected from the following: yellow plant-derived capsule shell, green plant-derived capsule shell, yellow gelatin capsule shell, green gelatin capsule shell. In addition, as for the color of the capsule shell, the wavelength range can be expanded to orange and blue.

To sum up, the CSDP capsule of the present invention can be useful in maintaining the stability of physicochemical properties and bio-active components of the CSDP.

EMBODIMENTS

The following experimental examples are offered only for the purpose of further illustrating the present invention.

Example 1

Preparation of Small Un-Coated CSDP (1) Formulation

| | |
|---|---|
| Radix salvia miltiorrhira | 41.06 g |
| Panax notoginseng | 8.03 g |
| Borneol | 0.46 g |
| Adjuvant PEG-6000 | 18 g |

One thousand dripping pills were prepared.

Extraction of *Radix salvia miltiorrhira* and *Panax notoginseng*:

Coarsely-ground *Radix salvia miltiorrhira* and *Panax notoginseng* were placed into an extraction tank, into which water with 5 times the weight of the *Radix salvia miltiorrhira* and *Panax notoginseng* crude drugs was poured to decoct for 2 hours. After filtration of the solution, the residue was continued to be extracted for the second time. In this extraction, water with 4 times the weight of the *Radix salvia miltiorrhira* and *Panax notoginseng* crude drugs was added into the residue to decoct for 1 hour. The solution was filtered and the residue was discarded. The filtrates obtained in the above twice extraction were combined and concentrated under a reduced pressure to obtain an extract with a relative density of 1.05. Then, 95% (v/v) ethanol was slowly added into the obtained extract solution to make a final ethanol content of 69%-71% (v/v), and allowed to stand still for 12 hours to separate the supernatant, and the supernatant was filtered. The filtrate was concentrated by recovering the ethanol to obtain an extract with a sugar degree of 50 brix (i.e. the *Radix salvia miltiorrhira* and *Panax notoginseng* extract).

The afore-obtained extract was weighted, and PEG-6000 with 2.5-3.5 times the weight of the extract was added into the extract and melted at a temperature of 85-90° C. Until being well-melted, the ground and screen-separated borneol was added into the melt according to the formula dosage. After homogenized mixing, the mixture was transferred to a dripping machine to drip at a temperature of 80-85° C. to give the un-coated CSDPs.

Finally, the un-coated CSDPs were loaded into the yellow plant-derived capsule shells with a corresponding wavelength of 586 nm.

Example 2

Preparation of Small Un-Coated CSDPs

Small un-coated CSDPs were prepared by the same drug ingredients and method as that in Example 1. The obtained pill was then loaded into the green plant-derived capsule shells with a corresponding wavelength of 572 nm.

Example 3

Preparation of Small Un-Coated CSDPs

Small un-coated CSDPs were prepared by the same drug ingredients and method as that in Example 1. The obtained pill was then loaded into the plant-derived capsule shells with a corresponding wavelength of 500 nm.

Example 4

Preparation of Small Un-Coated CSDPs

Small un-coated CSDPs were prepared by the same drug ingredients and method as that in Example 1. The obtained pill was then loaded into the yellow plant-derived capsule shells with a corresponding wavelength of 592 nm.

Example 5

Preparation of Small Un-Coated CSDPs

Small un-coated CSDPs were prepared by the same drug ingredients and method as that in Example 1. The obtained pill was then loaded into the plant-derived capsule shells with a corresponding wavelength of 577 nm.

Example 6

Preparation of Small Un-Coated CSDPs

Small un-coated CSDPs were prepared by the same drug ingredients and method as that in Example 1. The obtained pill was then loaded into the plant-derived capsule shells with a corresponding wavelength of 592 nm.

Example 7

Preparation of Small Un-Coated CSDPs

Small un-coated CSDPs were prepared by the same drug ingredients and method as that in Example 1. The obtained pill was then loaded into the orange plant-derived capsule shells with the corresponding wavelength of 620 nm.

Example 8

Preparation of Small Un-Coated CSDPs

Small un-coated CSDPs were prepared by the same drug ingredients and method as that in Example 1. The obtained pill was then loaded into the blue plant-derived capsule shells with a corresponding wavelength of 446 nm.

Example 9

Preparation of Small Un-Coated CSDPs

Small un-coated CSDPs were prepared by the same drug ingredients and method as that in Example 1. The obtained pill was then loaded into the yellow plant-derived capsule shells with a corresponding wavelength of 580 nm.

Example 10

Preparation of Small Un-Coated CSDPs

Small un-coated CSDPs were prepared by the same drug ingredients and method as that in Example 1. The obtained pill was then loaded into the blue plant-derived capsule shells with a corresponding wavelength of 460 nm.

Example 11

Preparation of Small Un-Coated CSDPs

Small un-coated CSDPs were prepared by the same drug ingredients and method as that in Example 1. The obtained pill was then loaded into the green plant-derived capsule shells with a corresponding wavelength of 550 nm.

Example 12

Preparation of Small Coated CSDPs (1) Formulation

| | |
|---|---|
| *Radix salvia miltiorrhira* | 41.06 g |
| *Panax notoginseng* | 8.03 g |
| Borneol | 0.46 g |
| Adjuvant PEG-6000 | 18 g |

One thousand dripping pills were prepared.

Extraction of *Radix salvia miltiorrhira* and *Panax notoginseng*:

Coarsely-ground *Radix salvia miltiorrhira* and *Panax notoginseng* were placed into an extraction tank, into which an aqueous solution of sodium hydroxide (pH 9) with 5 times the weight of the *Radix salvia miltiorrhira* and *Panax notoginseng* crude drugs was poured to decoct for 2 hours. After filtration of the solution, the residue was continued to be extracted for the second time. In this extraction, the aqueous solution of sodium hydroxide (pH 9) with 4 times the weight of the *Radix salvia miltiorrhira* and *Panax notoginseng* crude drugs was added to decoct for 1 hour. The solution was filtered and the residue was discarded. The filtrates obtained in the above twice extraction were combined and concentrated under a reduced pressure to an extract with a relative density of 1.25. Then, 95% (v/v) ethanol was slowly added into the obtained extract solution to make a final ethanol content of 69%-71% (v/v), and allowed to stand still for 12 hours to separate the supernatant, and the supernatant was filtered. The filtrate was concentrated by recovering ethanol to obtain an extract with a sugar degree of 90 brix (i.e. the *Radix salvia miltiorrhira* and *Panax notoginseng* extract).

The afore-obtained extract was weighted, and PEG-6000 with 2.5-3.5 times the weight of the extract was added into the extract and melted at a temperature of 85-90° C. Until being well-melted, the ground and screen-separated borneol was added into the melt according to the formula dosage. After homogenized mixing, the mixture was transferred to a dripping machine to drip at a temperature of 80-85° C. to give the small un-coated CSDPs.

Continuously, a gastric-soluble coating material was well dissolved in water. After homogenized mixing, the un-coated pills were transferred to a coating machine to conduct a coating operation under the coating conditions as follows according to a 6 wt % increase in weight after coating: an average inlet air temperature of 85° C., an average coating bed temperature of 35-38° C., a spraying pressure of 2 bar, an average rotating speed of 15-23 rpm and an average material flowing rate of 3-4 g/min to give the small coated CSDPs.

Finally, the coated CSDPs were loaded into the yellow plant-derived capsule shell with a corresponding wavelength of 586 nm.

Example 13

Preparation of Small Coated CSDPs

Small coated CSDPs were prepared by the same drug ingredients and method as that in Example 12. The obtained pill was then loaded into the green plant-derived capsule shells with a corresponding wavelength of 572 nm.

Example 14

Preparation of Small Coated CSDPs

Small coated CSDPs were prepared by the same drug ingredients and method as that in Example 12. The obtained pill was then loaded into the plant-derived capsule shells with a corresponding wavelength of 500 nm.

Example 15

Preparation of Small Coated CSDPs

Small coated CSDPs were prepared by the same drug ingredients and method as that in Example 12. The obtained pill was then loaded into the yellow plant-derived capsule shells with a corresponding wavelength of 592 nm.

Example 16

Preparation of Small Coated CSDPs

Small coated CSDPs were prepared by the same drug ingredients and method as that in Example 12. The obtained pill was then loaded into the plant-derived capsule shells with a corresponding wavelength of 577 nm.

Example 17

Preparation of Small Coated CSDPs

Small coated CSDPs were prepared by the same drug ingredients and method as that in Example 12. The obtained pill was then loaded into the plant-derived capsule shells with a corresponding wavelength of 592 nm.

Example 18

Preparation of Small Coated CSDP

Small coated CSDPs were prepared by the same drug ingredients and method as that in Example 12. The obtained pill was then loaded into the orange plant-derived capsule shells with a corresponding wavelength of 620 nm.

Example 19

Preparation of Small Coated CSDPs

Small coated CSDPs were prepared by the same drug ingredients and method as that in Example 12. The obtained pill was then loaded into the blue plant-derived capsule shells with a corresponding wavelength of 446 nm.

Example 20

Preparation of Small Coated CSDPs

Small coated CSDPs were prepared by the same drug ingredients and method as that in Example 12. The obtained pill was then loaded into the yellow plant-derived capsule shells with a corresponding wavelength of 580 nm.

Example 21

Preparation of Small Coated CSDPs

Small coated CSDPs were prepared by the same drug ingredients and method as that in Example 12. The obtained pill was then loaded into the blue plant-derived capsule shells with a corresponding wavelength of 460 nm.

Example 22

Preparation of Small Coated CSDPs

Small coated CSDPs were prepared by the same drug ingredients and method as that in Example 12. The obtained pill was then loaded into the green plant-derived capsule shells with a corresponding wavelength of 550 nm.

What is claimed is:

1. A capsule consisting of
a plant derived capsule shell; and
drug content, which is loaded into said capsule shell,
characterized in that said capsule shell is a colored shell and said drug content is compound danshen dripping pills comprising three traditional Chinese medicines of *Radix salvia miltiorrhira, Panax notoginseng* and borneol,
wherein said capsule shell is yellow or green in color with a corresponding wavelength in a range of 500-592 nm,
wherein said drug content comprises the following ingredients:
   (1) index ingredients in *Radix salvia miltiorrhira*: salvianic acid A, protocatechuic aldehyde, salvianolic acid L, salvianolic acid M, salvianolic acid D, rosmarinic acid, salvianolic acid B and salvianolic acid A;
   (2) index ingredients in *Panax notoginseng*: R1, Rg1+Re, Rb1, Rc, Rb2, Rb3 and Rd;
   (3) total phenolic acid, total saponin and total sugar; and
   (4) borneol
and wherein the wavelength range of said capsule shell is determined by using Data Envelopment Analysis (DEA) through intensive light exposure test and accelerated stability test.

2. The capsule according to claim 1, characterized in that said compound danshen dripping pills are coated or un-coated.

3. The capsule according to claim 1, characterized in that, relative to the total weight of three traditional Chinese medicines of *Radix salvia miltiorrhira, Panax notoginseng* and borneol, said compound danshen dripping pills are prepared from a formulation consisting of the crude drugs by the following weight percentages:

| | |
|---|---|
| *Radix salvia miltiorrhira* | 48.0%-97.0% |
| *Panax notoginseng* | 1.0%-50.0% |
| Borneol | 0.1%-3.0%. |

4. The capsule according to claim 1, characterized in that, relative to the total weight of three traditional Chinese medicines of *Radix salvia miltiorrhira, Panax notoginseng* and borneol, said compound danshen dripping pills are prepared from a formulation consisting of the crude drugs by the following weight percentages:

| | |
|---|---|
| *Radix salvia miltiorrhira* | 63.0%-94.0% |
| *Panax notoginseng* | 4.0%-35.0% |
| Borneol | 0.5%-2.0%. |

5. The capsule according to claim 1, characterized in that, relative to the total weight of three traditional Chinese medicine of *Radix salvia miltiorrhira, Panax notoginseng* and borneol, said compound danshen dripping pills are prepared from a formulation consisting of the crude drugs by the following weight percentages:

| | |
|---|---|
| *Radix salvia miltiorrhira* | 82.87% |
| *Panax notoginseng* | 16.21% |
| Borneol | 0.92%. |

6. The capsule according to claim 1, characterized in that said plant-derived capsule shell is made from pullulan or marine algal polysaccharide.

\* \* \* \* \*